United States Patent
Hayashi et al.

(10) Patent No.: US 11,401,502 B2
(45) Date of Patent: Aug. 2, 2022

(54) CELL POPULATION COMPRISING MESENCHYMAL STEM CELLS DERIVED FROM FETAL APPENDAGE, METHOD FOR PRODUCING THE SAME, AND PHARMACEUTICAL COMPOSITION

(71) Applicant: KANEKA CORPORATION, Osaka (JP)

(72) Inventors: Masahiro Hayashi, Hyogo (JP); Yuta Kita, Tokushima (JP); Nobuyoshi Umeda, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 477 days.

(21) Appl. No.: 16/461,218

(22) PCT Filed: Nov. 14, 2017

(86) PCT No.: PCT/JP2017/040923
§ 371 (c)(1),
(2) Date: May 15, 2019

(87) PCT Pub. No.: WO2018/092769
PCT Pub. Date: May 24, 2018

(65) Prior Publication Data
US 2019/0270964 A1 Sep. 5, 2019

(30) Foreign Application Priority Data
Nov. 15, 2016 (JP) .............................. JP2016-222243

(51) Int. Cl.
| | | |
|---|---|---|
| *C12N 5/073* | (2010.01) | |
| *A61K 35/50* | (2015.01) | |
| *G01N 33/50* | (2006.01) | |
| *A61P 43/00* | (2006.01) | |
| *G01N 33/53* | (2006.01) | |

(52) U.S. Cl.
CPC ............ *C12N 5/0605* (2013.01); *A61K 35/50* (2013.01); *A61P 43/00* (2018.01); *G01N 33/5005* (2013.01); *G01N 33/53* (2013.01); *G01N 2333/70596* (2013.01)

(58) Field of Classification Search
CPC .................................................... A61K 35/50
See application file for complete search history.

(56) References Cited

FOREIGN PATENT DOCUMENTS

| | | |
|---|---|---|
| JP | 2015-061520 A | 4/2015 |
| WO | 2013/077428 A1 | 5/2013 |

OTHER PUBLICATIONS

Wang et al., Stem Cells, 2004, 22:1330-1337.*
Fukuchi et al., Stem Cells, 2004, 22:649-658.*
Peltzer et al., Stem Cells and Development, 2015, 24(3):329-344.*
P. V. Guillot et al; "Intrauterine transplantation of human fetal mesenchymal stem cells from first-trimester blood repairs bone and reduces fractures in osteogenesis imperfecta mice", Blood, vol. 111, No. 3, Feb. 1, 2008; pp. 1717-1725 (9 pages).
L. Gucciardo et al; "Fetal mesenchymal stem cells: isolation, properties and potential use in perinatology and regenerative medicine", an International Journal of Obstetrics and Gynaecology, vol. 116, No. 2, Dec. 12, 2008; pp. 166-172 (7 pages).
M. Yu et al; "Mid-trimester fetal blood-derived adherent cells share characteristics similar to mesenchymal stem cells but full-term umbilical cord blood does not", British Journal of Haematology, vol. 124, No. 5, Mar. 1, 2004; pp. 666-675 (10 pages).
Extended European Search Report issued in corresponding European Application No. 17871312.9, dated Jun. 3, 2020 (7 pages).
Jeong Hee Moon et al.; "Successful vitrification of human-amnion-derived mesenchymal stem cells", Human Reproduction, vol. 23, No. 8, 2008; pp. 1760-1770 (11 pages).
Min-Soo Seo et al.; "Isolation and characterization of equine amniotic membrane-derived mesenchymal stem cells", Journal of Veterinary Science, vol. 14, No. 2, 2013; pp. 151-159 (9 pages).

* cited by examiner

*Primary Examiner* — Bin Shen
(74) *Attorney, Agent, or Firm* — Osha Bergman Watanabe & Burton LLP

(57) ABSTRACT

An object of the present invention is to provide highly proliferative mesenchymal stem cells (MSCs) useful for the large-scale and rapid production of a cell preparation, and a cell population comprising the mesenchymal stem cells. According to the present invention, there is provided a cell population comprising mesenchymal stem cells derived from the fetal appendage, wherein, in the cell population, the proportion of $CD105^+$ mesenchymal stem cells is 50% or more, the proportion of $CD200^+$ mesenchymal stem cells is less than 10%, and the proportion of $CD106^+$ mesenchymal stem cells is less than 5%.

4 Claims, 8 Drawing Sheets

[Fig. 1]
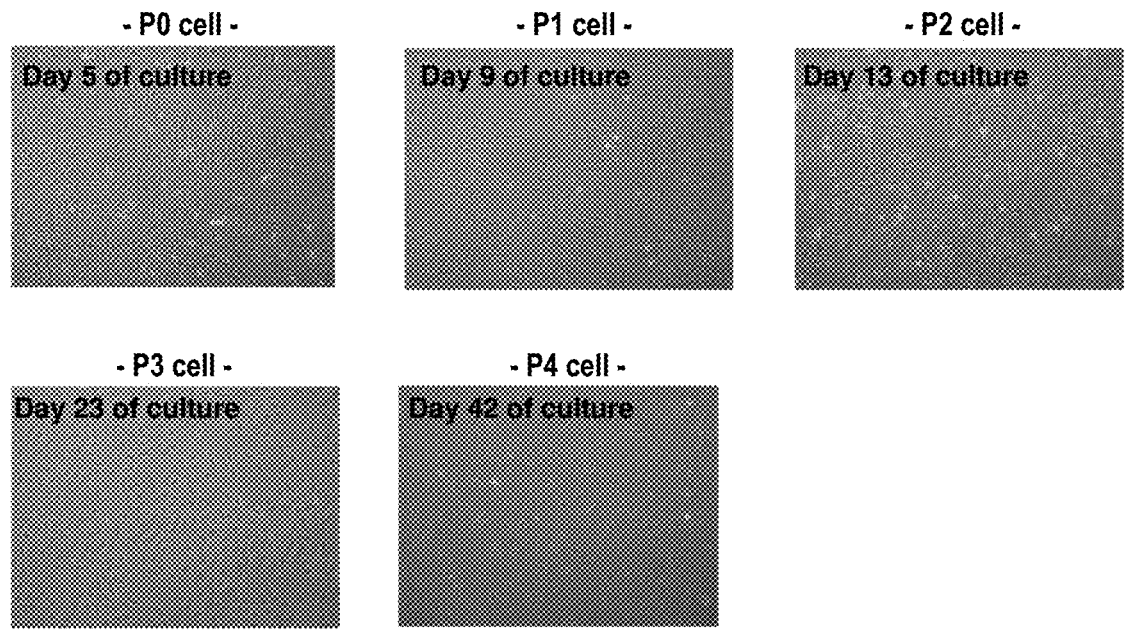
[Fig. 2]
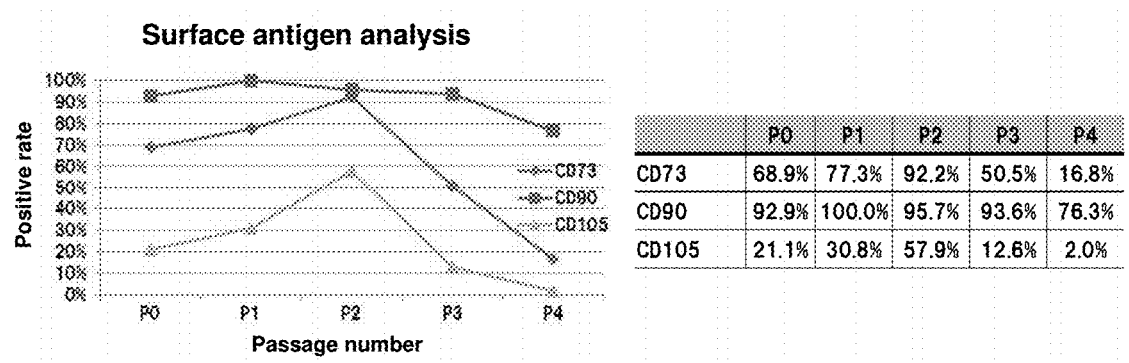

[Fig. 3]
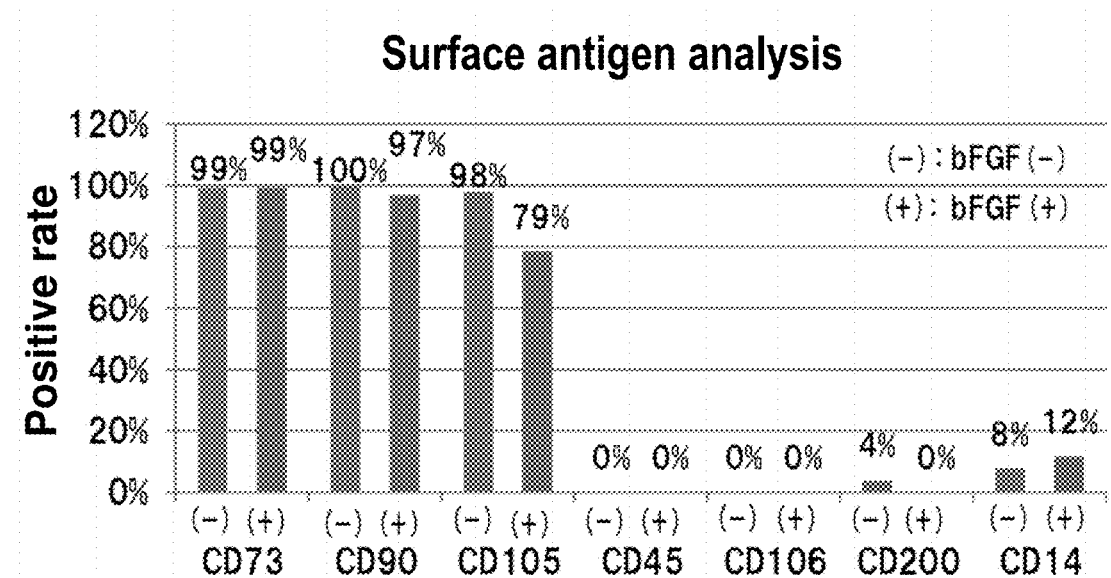
[Fig. 4]
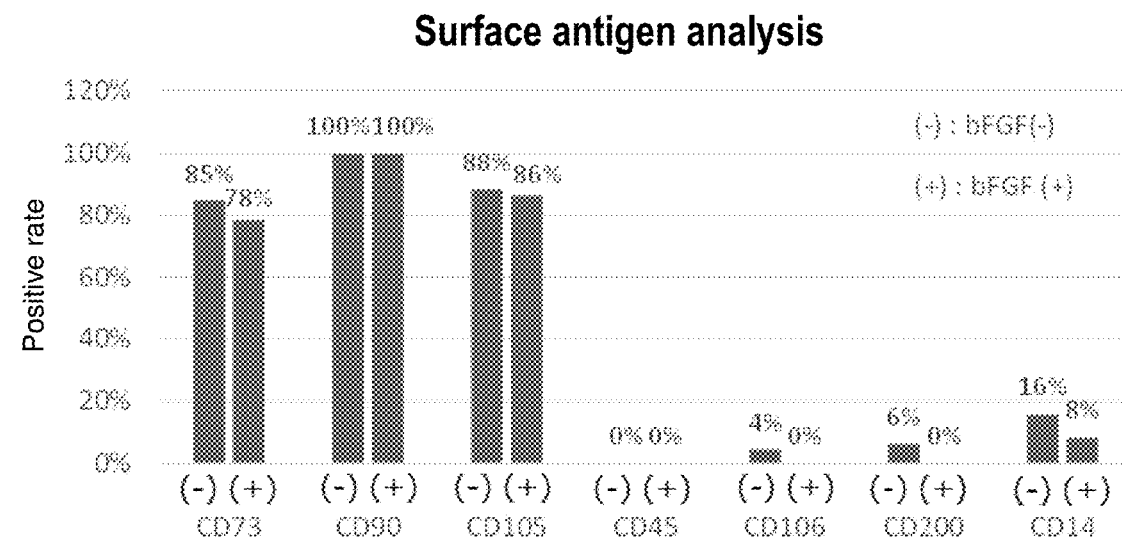

[Fig. 5]
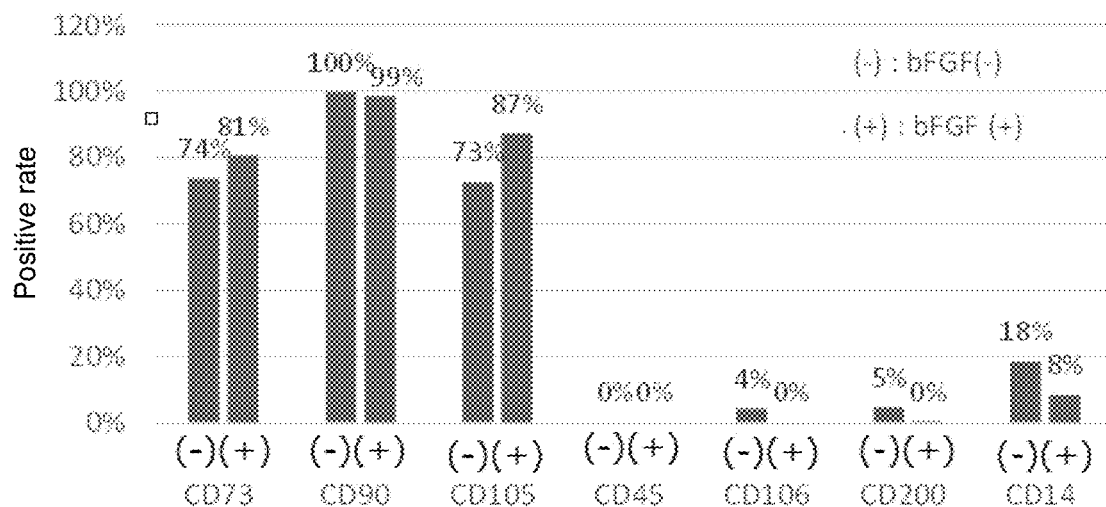
[Fig. 6]
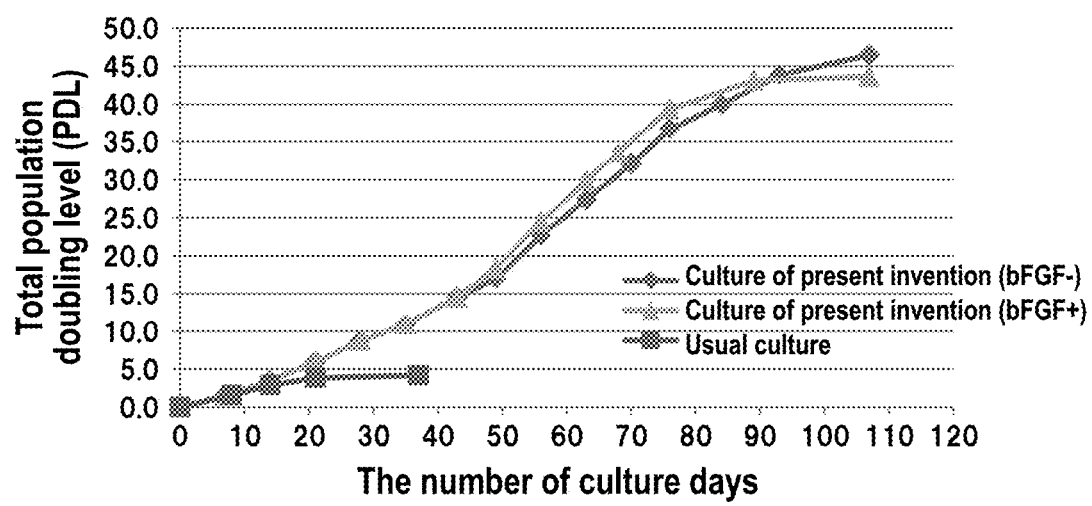

[Fig. 7]
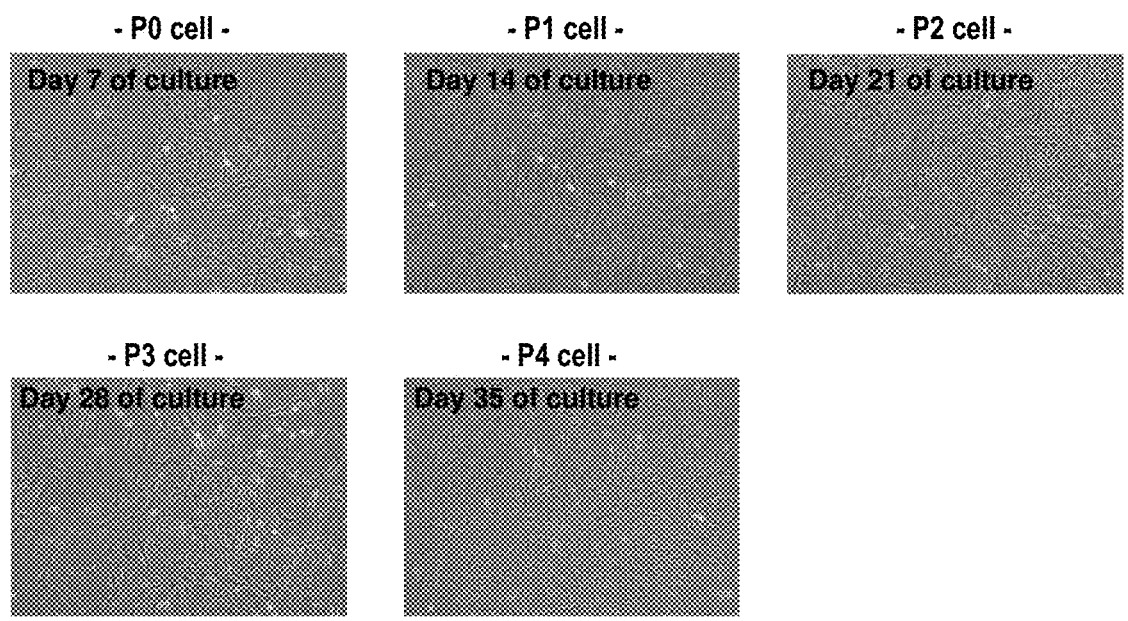
[Fig. 8]
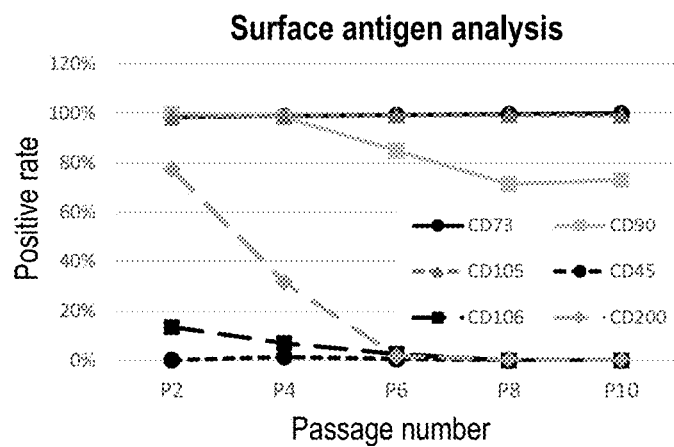

[Fig. 9]
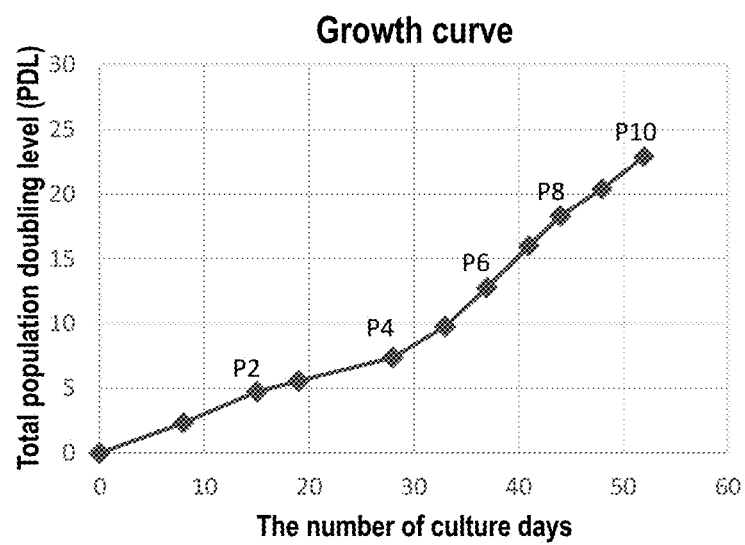

[Fig. 10]
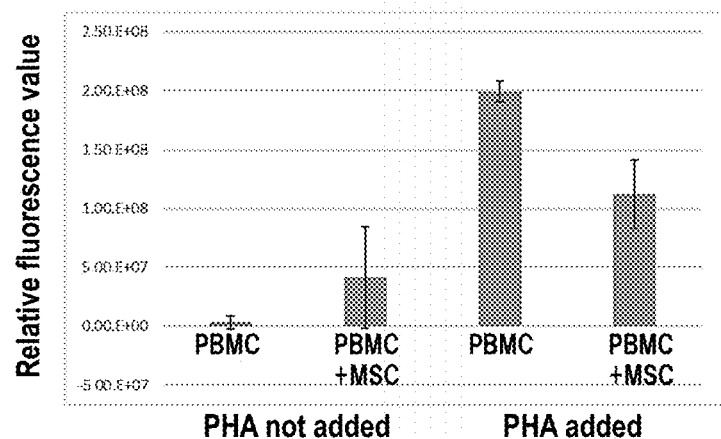

[Fig. 11]
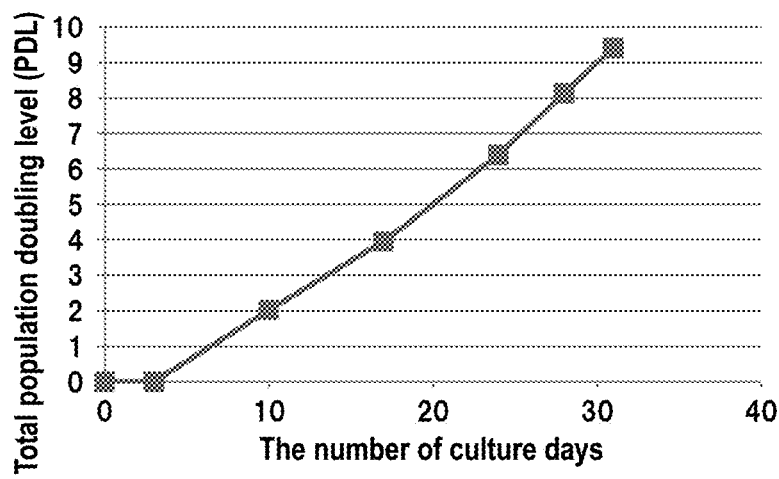
[Fig. 12]
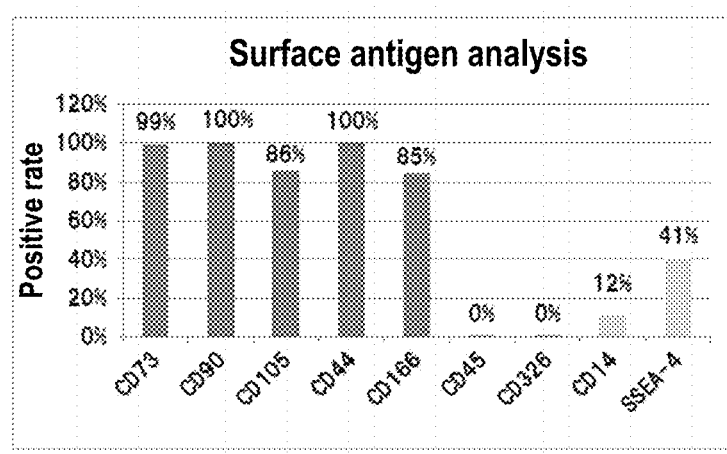
[Fig. 13]
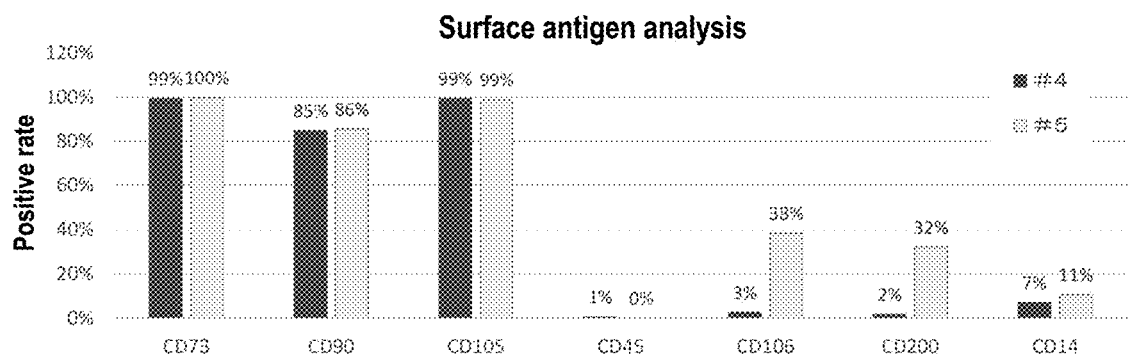

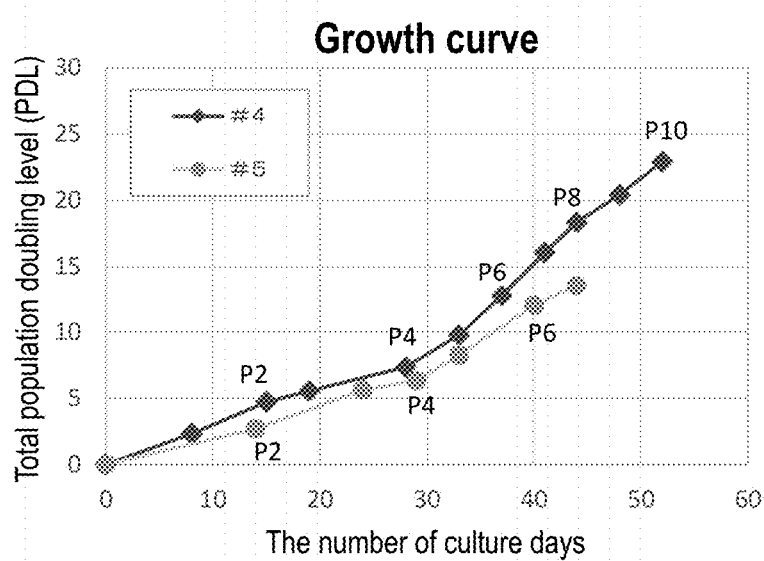
[Fig. 14]

CELL POPULATION COMPRISING MESENCHYMAL STEM CELLS DERIVED FROM FETAL APPENDAGE, METHOD FOR PRODUCING THE SAME, AND PHARMACEUTICAL COMPOSITION

CROSS-REFERENCE TO RELATED APPLICATION

The present application is based on and claims priority to Japanese Patent Application No. 2016-222243, filed on Nov. 15, 2016, and PCT Application No. PCT/JP2017/040923, filed on Nov. 14, 2017, the disclosure of which is hereby incorporated by reference in its entirety.

TECHNICAL FIELD

The present invention relates to a cell population comprising mesenchymal stem cells derived from the fetal appendage. The present invention relates to a method for producing the cell population, and a pharmaceutical composition comprising the cell population. The present invention further relates to a method for monitoring the proliferative properties of mesenchymal stem cells, a method for evaluating a donor and/or a sample collected from the donor, and a method for confirming and/or predicting enzyme treatment conditions, by utilizing the proportion of mesenchymal stem cells expressing a particular marker in the cell population as an index.

BACKGROUND ART

Mesenchymal stem cells, also called mesenchymal stromal cells, are somatic stem cells reported to exist in the bone marrow and the like, and are capable of differentiating into bones, cartilage, and fats, etc. Mesenchymal stem cells have been gaining attention as a potential cell source in cell therapy. Recently, it has been revealed that these cells also exist in the fetal appendage including the placenta, umbilical cord, and fetal membrane.

Mesenchymal stem cells have been gaining attention because of having immunosuppressive capacity as well as differentiation capacity, and are going into practical use for acute graft-versus-host disease (GVHD) and Crohn's disease which is an inflammatory bowel disease with the use of bone marrow mesenchymal stem cells. Various cells are known as mesenchymal stem cells. Among them, amniotic mesenchymal stem cells have a high immunosuppressive effect. Furthermore, the amnion which is a cell source is non-invasively collectable. Therefore, the application of the amniotic mesenchymal stem cells to cell therapy targeting various immune-related diseases is expected (Patent Document 1).

Patent Document 1 describes a method for producing an amniotic mesenchymal cell composition, a method for cryopreserving the composition, and a therapeutic agent. Particularly, this documents states that a mixture comprising amniotic mesenchymal cells is cryopreserved in a solution containing 5 to 10% by mass of dimethyl sulfoxide and containing 5 to 10% by mass of hydroxyethyl starch or 1 to 5% by mass of dextran such that the cryopreserved amniotic mesenchymal cells can be produced as a cell preparation optimized for transplantation. Patent Document 2 describes a method for preparing an amniotic mesenchymal stem cell population, comprising steps of: (D) collecting a cell population of mesenchymal cells from the amnion of a mammal; (E) seeding the collected cell population at a cell concentration of 400 to 35000 cells/cm$^2$, followed by initial culture for 2 to 3 days; (F) seeding the cultured cells at 1/5000 or more and less than 1/10 of the cell concentration of the initial culture, and repeating subculture three or four times with medium replacement twice a week; and (G) maintaining the culture of the cells in the same culture dish until confluent when a colony of cells having a fusiform form is formed in the subculture.

PRIOR ART DOCUMENTS

Patent Documents

Patent Document 1: JP Patent Publication (Kokai) No. 2015-61520 A (2015)
Patent Document 2: International Publication No. WO2013/077428

SUMMARY OF INVENTION

Object to be Solved by the Invention

The present inventors have confirmed by preliminary studies that amniotic mesenchymal stem cells are low proliferative and rarely proliferate with no increase in passage number or population doubling level after 3 passages. Hence, the large-scale and rapid preparation or production of cells necessary for cell formulation has been found to be not always easy. Patent Document 1 states that a mixture comprising amniotic mesenchymal cells is cryopreserved in a particular cryopreservation solution such that decrease in the survival rate of amniotic mesenchymal cells after thawing can be prevented, and the cryopreserved amniotic mesenchymal cells can be produced as a cell preparation optimized for transplantation. However, this document makes no mention about the selective preparation of mesenchymal stem cells having a particular excellent feature from among mesenchymal stem cells, specifically, the selective preparation of a cell population rich in highly proliferative mesenchymal stem cells useful for the large-scale and rapid production of a cell preparation by utilizing the characteristics of mesenchymal stem cells as an index. In Patent Document 2, a mesenchymal stem cell population having high proliferative capacity and differentiation capacity is prepared by seeding cells at a low density. However, this document neither describes nor suggests a culture method for maintaining high proliferative properties by utilizing the characteristics of mesenchymal stem cells comprised in a mesenchymal stem cell population as an index, and a cell population rich in highly proliferative mesenchymal stem cells having the characteristics of mesenchymal stem cells.

An object of the present invention is to provide highly proliferative mesenchymal stem cells (MSCs) useful for the large-scale and rapid production of a cell preparation, a cell population comprising the mesenchymal stem cells, a method for producing the same, and a pharmaceutical composition comprising the cell population. A further object of the present invention is to provide a method for monitoring the proliferative properties of mesenchymal stem cells, a method for evaluating a donor and/or a sample collected from the donor, and a method for determining and/or predicting optimum enzyme treatment conditions, by utilizing an index related to cell populations comprising mesenchymal stem cells.

Means for Solving the Object

As a result of intensive studies in order to achieve the above objects, the present inventors found that a cell population comprising mesenchymal stem cells that always exhibit high proliferative properties can be obtained by culture under conditions that maintain the proportion of $CD105^+$ mesenchymal stem cells which is equal to or more than a predetermined value and the proportion of $CD200^+$ mesenchymal stem cells and the proportion of $CD106^+$ mesenchymal stem cells which are less than their respective predetermined values in a cell population comprising cells collected from the fetal appendage. The present inventors further found that: the proliferative properties of mesenchymal stem cells can be monitored by utilizing, as an index, the proportion of $CD105^+$ mesenchymal stem cells which is equal to or more than a predetermined value and the proportion of $CD200^+$ mesenchymal stem cells and the proportion of $CD106^+$ mesenchymal stem cells which are less than their respective predetermined values in a cell population comprising mesenchymal stem cells collected from the fetal appendage; the quality of a donor and/or a sample collected from the donor can be evaluated by utilizing this index, from the viewpoint of efficiently obtaining highly proliferative mesenchymal stem cells; and enzyme treatment conditions optimum for the sample collected from the donor can be determined and/or predicted by utilizing this index. The present invention has been completed on the basis of these findings.

Specifically, the present specification provides the following aspects of the invention:

(1) A cell population comprising mesenchymal stem cells derived from the fetal appendage, wherein in the cell population, the proportion of $CD105^+$ mesenchymal stem cells is 50% or more, the proportion of $CD200^+$ mesenchymal stem cells is less than 10%, and the proportion of $CD106^+$ mesenchymal stem cells is less than 5%.

(2) The cell population according to (1), wherein the cell population comprises at least $CD14^+$ mesenchymal stem cells.

(3) The cell population according to (2), wherein in the cell population, the proportion of the $CD14^+$ mesenchymal stem cells is 5% or more.

(4) The cell population according to any one of (1) to (3), wherein the mesenchymal stem cells are culturable without the arrest of proliferation up to 40 days or later after the start of ex vivo culture.

(4-1) The cell population according to any one of (1) to (4), wherein the mesenchymal stem cells are culturable without the arrest of proliferation up to 70 days or later after the start of ex vivo culture.

(5) The cell population according to any one of (1) to (4) and (4-1), wherein the mesenchymal stem cells are culturable up to a population doubling level of 10 or more after the start of ex vivo culture.

(5-1) The cell population according to any one of (1) to (4), (4-1) and (5), wherein the mesenchymal stem cells are culturable up to a population doubling level of 30 or more after the start of ex vivo culture.

(6) The cell population according to any one of (1) to (4), (4-1), (5) and (5-1), wherein a population doubling time of the mesenchymal stem cells is 2 days or shorter.

(7) A pharmaceutical composition comprising the cell population according to any one of (1) to (4), (4-1), (5), (5-1) and (6) and a pharmaceutically acceptable carrier.

(8) A method for producing a cell population comprising mesenchymal stem cells derived from the fetal appendage, the method comprising a step of culturing a cell population comprising cells collected from the fetal appendage under conditions that maintain the proportion of $CD105^+$ mesenchymal stem cells in the cell population which is 50% or more, the proportion of $CD200^+$ mesenchymal stem cells in the cell population which is less than 10%, and the proportion of $CD106^+$ mesenchymal stem cells in the cell population which is less than 5%.

(9) The method for producing a cell population according to (8), wherein the cell population comprising cells collected from the fetal appendage is a cell population obtained by treating a sample comprising an epithelial cell layer and a mesenchymal stem cell layer collected from the fetal appendage with at least collagenase.

(10) The method for producing a cell population according to (8) or (9), further comprising a step of repeating a plurality of times the seeding of the cell population comprising cells collected from the fetal appendage at a density of 400 to 5,000 cells/cm$^2$, followed by culture.

(11) The method for producing a cell population according to (10), wherein the culture period of time is 4 to 10 days.

(12) A method for monitoring the proliferative properties of mesenchymal stem cells, comprising measuring the proportion of $CD105^+$ mesenchymal stem cells, the proportion of $CD200^+$ mesenchymal stem cells and the proportion of $CD106^+$ mesenchymal stem cells in a cell population comprising mesenchymal stem cells derived from the fetal appendage, and monitoring the proliferative properties of the mesenchymal stem cells by utilizing, as an index, the proportion of $CD105^+$ mesenchymal stem cells in the cell population which is 50% or more, the proportion of $CD200^+$ mesenchymal stem cells in the cell population which is less than 10%, and the proportion of $CD106^+$ mesenchymal stem cells in the cell population which is less than 5%.

(12-1) The method according to (12), further comprising measuring the proportion of $CD14^+$ mesenchymal stem cells in the cell population, and monitoring the proliferative properties of the mesenchymal stem cells by utilizing, as an index, the proportion of $CD14^+$ mesenchymal stem cells in the cell population which is 5% or more.

(13) A method for evaluating a donor and/or a sample collected from the donor, comprising collecting a cell population comprising mesenchymal stem cells derived from the fetal appendage from the donor, measuring the proportion of $CD105^+$ mesenchymal stem cells, the proportion of $CD200^+$ mesenchymal stem cells and the proportion of $CD106^+$ mesenchymal stem cells, and making evaluation by utilizing, as an index, the proportion of $CD105^+$ mesenchymal stem cells in the cell population which is 50% or more, the proportion of $CD200^+$ mesenchymal stem cells in the cell population which is less than 10%, and the proportion of $CD106^+$ mesenchymal stem cells in the cell population which is less than 5%.

(13-1) The method for evaluating a donor and/or a sample collected from the donor according to (13), further comprising measuring the proportion of $CD14^+$ mesenchymal stem cells in the cell population, and making evaluation by utilizing, as an index, the proportion of $CD14^+$ mesenchymal stem cells in the cell population which is 5% or more.

(14) A method for determining and/or predicting enzyme treatment conditions optimum for a sample collected from a donor, comprising measuring the proportion of $CD105^+$ mesenchymal stem cells, the proportion of $CD200^+$ mesenchymal stem cells and the proportion of $CD106^+$ mesenchymal stem cells in a cell population obtained by the enzyme treatment of the sample, and making evaluation by utilizing, as an index, the proportion of $CD105^+$ mesenchymal stem cells in the cell population which is 50% or more, the proportion of $CD200^+$ mesenchymal stem cells in the cell population which is less than 10%, and the proportion of CD106$^+$ mesenchymal stem cells in the cell population which is less than 5%.

(14-1) The method for determining and/or predicting enzyme treatment conditions optimum for a sample according to (14), further comprising measuring the proportion of CD14$^+$ mesenchymal stem cells in the cell population, and making evaluation by utilizing, as an index, the proportion of CD14$^+$ mesenchymal stem cells in the cell population which is 5% or more.

Advantageous Effects of Invention

According to the present invention, a cell population comprising highly proliferative mesenchymal stem cells can be obtained. According to the present invention, the positive rates of various surface antigens can be utilized as an index for the formation of a cell population comprising highly proliferative mesenchymal stem cells. This enables large-scale and rapid production of a cell preparation (pharmaceutical composition). According to the present invention, the proliferative properties of mesenchymal stem cells can be monitored by utilizing, as an index, the proportion of CD105$^+$ mesenchymal stem cells in the cell population which is 50% or more, the proportion of CD200$^+$ mesenchymal stem cells in the cell population which is less than 10%, and the proportion of CD106$^+$ mesenchymal stem cells in the cell population which is less than 5%. Particularly, changes in the proliferative properties of mesenchymal stem cells can be rapidly grasped and predicted by measuring the index over time. According to the present invention, the quality of a donor itself and/or a sample collected from the donor can be evaluated by utilizing the index. According to the present invention, whether an enzyme treatment method is optimum for the enzyme treatment of the sample collected from the donor can be determined and/or predicted by utilizing the index.

BRIEF DESCRIPTION OF DRAWINGS

FIG. 1 shows photographs of cells when amniotic MSCs were subcultured (usual culture).

FIG. 2 shows results of analyzing the positive rates of various surface antigens (CD73, CD90, and CD105) using a flow cytometer as to amniotic MSCs on a passage basis obtained by subculture (usual culture).

FIG. 3 shows results of analyzing the positive rates of various surface antigens (CD73, CD90, CD105, CD45, CD106, CD200, and CD14) using a flow cytometer as to amniotic MSCs of the 7th passage in the culture according to the present invention.

FIG. 4 shows results of analyzing the positive rates of various surface antigens (CD73, CD90, CD105, CD45, CD106, CD200, and CD14) using a flow cytometer as to amniotic MSCs of the 9th passage in the culture according to the present invention.

FIG. 5 shows results of analyzing the positive rates of various surface antigens (CD73, CD90, CD105, CD45, CD106, CD200, and CD14) using a flow cytometer as to amniotic MSCs of the 11th passage in the culture according to the present invention.

FIG. 6 shows the growth curve of amniotic MSCs when the amniotic MSCs were cultured by usual culture or by the culture according to the present invention.

FIG. 7 shows photographs of cells when amniotic MSCs were subcultured by the culture according to the present invention.

FIG. 8 shows results of analyzing the positive rates of various surface antigens (CD73, CD90, CD105, CD45, CD106, and CD200) using a flow cytometer as to amniotic MSCs of the 2nd, 4th, 6th, 8th and 10th passages in the culture according to the present invention.

FIG. 9 shows the growth curve of the amniotic MSCs obtained in FIG. 8.

FIG. 10 shows results of studying the immunomodulatory effect of amniotic MSCs obtained by the culture according to the present invention.

FIG. 11 shows the growth curve of amniotic MSCs enzyme-treated by the method of the present invention.

FIG. 12 shows results of analyzing the positive rates of various surface antigens (CD73, CD90, CD105, CD44, CD166, CD45, CD326, CD14, and SSEA-4) using a flow cytometer as to amniotic MSCs of the 9th passage in culture by a method described in claim 7 of International Publication No. WO2013/077428 after the enzyme treatment according to the present invention.

FIG. 13 shows results of analyzing the positive rates of various surface antigens (CD73, CD90, CD105, CD45, CD106, and CD200) using flow cytometry as to amniotic MSCs of the 6th passage when amniotic MSCs (#4 and #5) obtained from different donors were subcultured by the culture of the present invention.

FIG. 14 shows the growth curve of amniotic MSCs when amniotic MSCs #4 and #5 from different donors were cultured by the culture according to the present invention.

EMBODIMENT OF CARRYING OUT THE INVENTION

Embodiments of the present invention are specifically explained below. However, these embodiments are intended to facilitate understanding of the principles of the present invention, and therefore, the scope of the present invention is not limited to the embodiments. Other embodiments with appropriate modifications made by a person skilled in the art are also included in the scope.

[1] Explanation of Terms

The term "fetal appendage" used herein refers to a fetal membrane, a placenta, an umbilical cord, and amniotic fluid. In addition, the term "fetal membrane" refers to a fetal sac containing fetal amniotic fluid, which comprises an amnion, a chorion, and a decidua in that order from the inside. Among them, the amnion and the chorion are originated from the fetus. The term "amnion" refers to a transparent thin membrane with few blood vessels, which is located in the most inner layer of the fetal membrane. The inner layer (also called epithelial cell layer) of the amnion is covered with a layer of epithelial cells having a secretory function and secretes amniotic fluid. The outer layer (also called extracellular matrix layer, which corresponds to the stroma) of the amnion comprises mesenchymal stem cells.

The term "mesenchymal stromal cells (MSCs)" used herein refers to stem cells that satisfy conditions described below, and are used interchangeably with "mesenchymal stromal cells". The term "mesenchymal stem cells" is also described as "MSCs".

Definition of Mesenchymal Stem Cells
i) Adherence to plastic in standard medium under culture conditions
ii) Positive for surface antigens CD105, CD73, and CD90, and negative for surface antigens CD45, CD34, CD11b, CD79alpha, CD19, and HLA-DR The term "amniotic mesenchymal stem cells" used herein refers to mesenchymal stem cells derived from the amnion, and are used interchangeably with "amniotic mesenchymal stromal cells". The term "amniotic mesenchymal stem cells" used herein is also described as "amniotic MSCs".

The term "mesenchymal stem cell population" used herein means a cell population comprising mesenchymal stem cells. Examples of the form thereof include, but are not particularly limited to, cell pellets, cell aggregates, cell-floated liquids and cell suspensions.

The term "proliferative capacity" used herein refers to the ability of cells to increase a cell count by cell division. The term "high proliferative capacity" used herein can be used interchangeably with "high proliferative properties". The proliferative capacity of amniotic mesenchymal stem cells (amniotic MSCs) in an amniotic mesenchymal stem cell population can be evaluated using an obtained cell count per batch of culture, a growth rate, a population doubling level, a population doubling time and/or a passage number.

The phrase "proportion of mesenchymal stem cells presenting a surface antigen selected from $CD105^+$, $CD200^+$, $CD106^+$, $CD14^+$, $CD73^+$, $CD90^+$, and $CD45^+$ in a cell population" used herein refers to the proportion of cells positive for the surface antigen analyzed by flow cytometry as described in Examples mentioned later. The phrase "proportion of cells positive for the surface antigen" used herein is also described as "positive rate".

[2] Cell Population Comprising Mesenchymal Stem Cells Derived from Fetal Appendage A feature of the cell population comprising mesenchymal stem cells derived from the fetal appendage, provided by the present invention is that in the cell population, the proportion of $CD105^+$ mesenchymal stem cells is 50% or more, the proportion of $CD200^+$ mesenchymal stem cells is less than 10%, and the proportion of $CD106^+$ mesenchymal stem cells is less than 5%.

Also, the cell population comprising mesenchymal stem cells derived from the fetal appendage, provided by the present invention forms a cell population comprising highly proliferative mesenchymal stem cells when satisfying conditions involving the proportion of $CD105^+$ mesenchymal stem cells which is 50% or more, the proportion of $CD200^+$ mesenchymal stem cells which is less than 10%, and the proportion of $CD106^+$ mesenchymal stem cells which is less than 5%. Hence, in the present invention, the conditions can be utilized as an index for the formation of a cell population comprising mesenchymal stem cells having highly proliferative properties or high proliferative capacity. Furthermore, changes in the proliferative properties of mesenchymal stem cells can be rapidly grasped and predicted by measuring the index over time. According to the present invention, the quality of a donor itself and/or a sample collected from the donor can be evaluated by utilizing the index. According to the present invention, whether an enzyme treatment method is optimum for the enzyme treatment of the sample collected from the donor can be determined and/or predicted by utilizing the index.

In the cell population, the proportion of the $CD105^+$ mesenchymal stem cells is preferably 55% or more, more preferably 60% or more, further preferably 65% or more, further preferably 70% or more, further preferably 75% or more, further preferably 80% or more, further preferably 85% or more, further preferably 90% or more, further preferably 95% or more, further preferably 96% or more, further preferably 97% or more, and further preferably 98% or more.

In the cell population, the proportion of the $CD200^+$ mesenchymal stem cells is preferably 9% or less, more preferably 8% or less, further preferably 7% or less, further preferably 6% or less, further preferably 5% or less, and further preferably 4% or less.

In the cell population, the proportion of the $CD106^+$ mesenchymal stem cells is preferably 4% or less, more preferably 3% or less, further preferably 2% or less, further preferably 1% or less, and further preferably 0%.

The cell population of the present invention may preferably comprise at least $CD14^+$ mesenchymal stem cells. When the cell population of the present invention comprises $CD14^+$ mesenchymal stem cells, the proportion of the $CD14^+$ mesenchymal stem cells in the cell population is preferably 5% or more, more preferably 6% or more, further preferably 7% or more, and further preferably 8% or more.

In the cell population, the proportion of $CD73^+$ mesenchymal stem cells is preferably 55% or more, more preferably 60% or more, further preferably 65% or more, further preferably 70% or more, further preferably 75% or more, further preferably 80% or more, further preferably 85% or more, further preferably 90% or more, further preferably 95% or more, further preferably 96% or more, further preferably 97% or more, further preferably 98% or more, and further preferably 99% or more.

In the cell population, the proportion of $CD90^+$ mesenchymal stem cells is preferably 55% or more, more preferably 60% or more, further preferably 65% or more, further preferably 70% or more, further preferably 75% or more, further preferably 80% or more, further preferably 85% or more, further preferably 90% or more, further preferably 95% or more, further preferably 96% or more, further preferably 97% or more, further preferably 98% or more, further preferably 99% or more, and further preferably 100%.

In the cell population, the proportion of $CD45^+$ mesenchymal stem cells is preferably 10% or less, more preferably 9% or less, further preferably 8% or less, further preferably 7% or less, further preferably 6% or less, further preferably 5% or less, further preferably 4% or less, further preferably 3% or less, further preferably 2% or less, further preferably 1% or less, and further preferably 0%.

In the present invention, $CD105^+$, $CD200^+$, $CD106^+$, $CD14^+$, $CD73^+$, $CD90^+$, and $CD45^+$ mean being positive for the expression of CD105, CD200, CD106, CD14, CD73, CD90, and CD45, respectively. $CD105^+$, $CD200^+$, $CD106^+$, $CD14^+$, $CD73^+$, $CD90^+$, or $CD45^+$ cells mean that the cells are found to be positive for the expression of each of these expression markers.

The expression markers (CD105, CD200, CD106, CD14, CD73, CD90, and CD45) can be detected by any detection method known in the art. Examples of the method for detecting the expression markers include, but are not limited to, flow cytometry and cell staining. When cells that emit stronger fluorescence as compared with a negative control (isotype control) are detected in flow cytometry using a fluorescently labeled antibody, the cells are confirmed to be "positive" for the marker. Any antibody known in the art can be used as the fluorescently labeled antibody. Examples thereof include, but are not limited to, antibodies labeled with fluorescein isothiocyanate (FITC), phycoerythrin (PE), allophycocyanin (APC), or the like. When cells that are stained or emit fluorescence are observed under a microscope in cell staining, the cells are confirmed to be "positive" for the marker. The cell staining may be cell immunostaining using an antibody, or may be non-immune cell staining using no antibody.

In the cell population of the present invention, the mesenchymal stem cells are culturable without the arrest of proliferation preferably up to 40 days or later, and more preferably up to 45 days or later, up to 50 days or later, up to 55 days or later, up to 60 days or later, up to 65 days or later, up to 70 days or later, up to 75 days or later, up to 80 days or later, up to 85 days or later, up to 90 days or later, up to 95 days or later, up to 100 days or later, up to 105 days or later, or up to 110 days or later, after the start of ex vivo culture.

In the cell population of the present invention, the mesenchymal stem cells are culturable up to a population doubling level of preferably 10 or more, and more preferably 15 or more, 20 or more, 25 or more, 30 or more, 35 or more, 40 or more, 45 or more, or 50 or more, after the start of ex vivo culture.

The population doubling level is the number of times of division of cells in a certain culture period of time and is calculated according to the expression [$\log_{10}$(Cell count at the completion of culture)–$\log_{10}$(Cell count at the start of culture)]/$\log_{10}$ (2). In the case of performing passages, the respective population doubling levels of passage numbers are calculated according to the expression and then cumulated to calculate a total population doubling level.

In the cell population of the present invention, the possible passage number of the mesenchymal stem cells is 1 or more, preferably 2 or more, more preferably 3 or more, further preferably 4 or more, further preferably 5 or more, further preferably 6 or more, further preferably 7 or more, further preferably 8 or more, further preferably 9 or more, further preferably 10 or more, further preferably 11 or more, further preferably 12 or more, further preferably 13 or more, further preferably 14 or more, further preferably 15 or more, further preferably 16 or more, further preferably 17 or more, further preferably 18 or more, further preferably 19 or more, further preferably 20 or more, and further preferably 25 or more. The upper limit of the possible passage number is not particularly limited and is, for example, 50 or less, 45 or less, 40 or less, 35 or less or 30 or less.

In the cell population of the present invention, the population doubling time is the number of days or the time required for the doubling of cells and is calculated by dividing the number of culture days or the culture time by the population doubling level. For example, the population doubling time at the 6th passage is calculated by dividing the number of days from the seeding to recovery of cells of the 6th passage by the population doubling level from the seeding to recovery of cells of the 6th passage. Time-dependent changes in the growth rate of cells can be evaluated by calculating the population doubling time per passage on a passage basis. In the present specification, the population doubling time is 2 days or shorter, preferably 1.9 days or shorter, more preferably 1.8 days or shorter, further preferably 1.7 days or shorter, further preferably 1.6 days or shorter, further preferably 1.5 days or shorter, further preferably 1.4 days or shorter, further preferably 1.3 days or shorter, further preferably 1.2 days or shorter, further preferably 1.1 days or shorter, and further preferably 1 day or shorter.

The mesenchymal stem cell population of the present invention can be preserved in a frozen state until immediately before use. The mesenchymal stem cell population may comprise any component, in addition to the mesenchymal stem cells. Examples of such a component can include, but are not limited to, salts, polysaccharides (e.g., HES and dextran), proteins (e.g., albumin), DMSO, and medium components (e.g., components contained in RPMI1640 medium).

[3] Method for Producing Cell Population Comprising Mesenchymal Stem Cells

The method for producing a cell population comprising mesenchymal stem cells derived from the fetal appendage according to the present invention is a method comprising a step of culturing a cell population comprising cells collected from the fetal appendage under conditions that maintain the proportion of $CD105^+$ mesenchymal stem cells in the cell population which is 50% or more, the proportion of $CD200^+$ mesenchymal stem cells in the cell population which is less than 10%, and the proportion of $CD106^+$ mesenchymal stem cells in the cell population which is less than 5%.

The conditions serve as an index for the formation of a cell population comprising highly proliferative mesenchymal stem cells. The culture method of the present invention is not particularly limited as long as the index is satisfied.

The production method of the present invention may comprise a cell population obtainment step of obtaining a cell population comprising mesenchymal stem cells by the enzyme treatment of the fetal appendage such as the amnion.

The amnion comprises an epithelial cell layer and an extracellular matrix layer. The latter layer comprises amniotic MSCs. Like other epithelial cells, the amniotic epithelial cells are characterized in that they express epithelial cadherin (E-cadherin: CD324) and an epithelial cell adhesion factor (EpCAM: CD326) while the amniotic MSCs do not express such epithelial-specific surface antigen markers. Thus, these cells can be easily distinguished by flow cytometry. The cell population obtainment step may be a step comprising a step of obtaining the amnion by cesarean section.

The cell population comprising cells collected from the fetal appendage according to the present invention is preferably a cell population obtained by treating a sample comprising an epithelial cell layer and a mesenchymal stem cell layer collected from the fetal appendage with at least collagenase.

The enzyme treatment of the sample collected from the fetal appendage (preferably a sample comprising an epithelial cell layer and a mesenchymal stem cell layer) is preferably a treatment with an enzyme (or a combination of enzymes) that can release mesenchymal stem cells contained in the extracellular matrix layer of the fetal appendage, and does not degrade the epithelial cell layer. Examples of such an enzyme can include, but are not particularly limited to, collagenase and/or metalloproteinase. Examples of the metalloproteinase can include, but are not particularly limited to, thermolysin and/or dispase, which is metalloproteinase that cleaves nonpolar amino acids at their N-terminal sides The active concentration of the collagenase is preferably 50 PU/ml or higher, more preferably 100 PU/ml or higher, further preferably 200 PU/ml or higher, further preferably 300 PU/ml or higher, and further preferably 400 PU/ml or higher. The active concentration of the collagenase is, but is not particularly limited to, for example, 1000 PU/ml or lower, 900 PU/ml or lower, 800 PU/ml or lower, 700 PU/ml or lower, 600 PU/ml or lower, or 500 PU/ml or lower. In this context, PU (protease unit) is defined as the amount of the enzyme that degrades 1 ug of FITC-collagen for 1 minute at 30° C. at pH 7.5.

The active concentration of the metalloproteinase (e.g., thermolysin and/or dispase) is preferably 50 PU/ml or higher, more preferably 100 PU/ml or higher, further preferably 200 PU/ml or higher, further preferably 300 PU/ml or higher, and further preferably 400 PU/ml or higher. Also, the active concentration of the metalloproteinase is preferably 1000 PU/ml or lower, more preferably 900 PU/ml or lower, further preferably 800 PU/ml or lower, further preferably 700 PU/ml or lower, further preferably 600 PU/ml or lower, and further preferably 500 PU/ml or lower. In this context, PU (protease unit) in an aspect of using dispase as the metalloproteinase is defined as the amount of the enzyme that releases an amino acid corresponding to 1 ug tyrosine from casein lactate for 1 minute at 30° C. at pH 7.5. In the concentration range of the enzyme described above, mesenchymal stem cells contained in the extracellular matrix layer can be efficiently released while prevented from being contaminated with epithelial cells contained in the epithelial cell layer of the fetal appendage. The preferred combination of the concentrations of the collagenase and/or the metalloproteinase can be determined by the microscopic observation of the fetal appendage after the enzyme treatment, or the flow cytometry of the obtained cells.

It is preferred to treat the fetal appendage with collagenase and metalloproteinase in combination, from the viewpoint of efficiently recovering live cells. Further preferably, the fetal appendage is treated with the combination at the same time in one operation. In this case, thermolysin and/or dispase can be used as the metalloproteinase, though the metalloproteinase is not limited thereto. The fetal appendage can be treated only once with an enzyme solution containing collagenase and metalloproteinase to conveniently obtain mesenchymal stem cells. The treatment at the same time in one operation can reduce the risk of contamination by bacteria, viruses, and the like.

For the enzyme treatment of the fetal appendage, it is preferred to dip, in the enzyme solution, the amnion washed using a washing solution such as physiological saline or Hank's balanced salt solution, and perform the treatment with stirring using stirring means. A stirrer or a shaker can be used as such stirring means from the viewpoint of efficiently releasing mesenchymal stem cells contained in the extracellular matrix layer of the fetal appendage, though the stirring means is not limited thereto. The stirring rate is not particularly limited and is, in the case of using a stirrer or a shaker, for example, 5 rpm or more, 10 rpm or more, 20 rpm or more, 30 rpm or more, 40 rpm or more or 50 rpm or more. Also, the stirring rate is not particularly limited and is, in the case of using a stirrer or a shaker, for example, 100 rpm or less, 90 rpm or less, 80 rpm or less, 70 rpm or less or 60 rpm or less. The enzyme treatment time is not particularly limited and is, for example, 10 minutes or longer, 20 minutes or longer, 30 minutes or longer, 40 minutes or longer, 50 minutes or longer, 60 minutes or longer, 70 minutes or longer, 80 minutes or longer or 90 minutes or longer. Also, the enzyme treatment time is not particularly limited and is, for example, 6 hours or shorter, 5 hours or shorter, 4 hours or shorter, 3 hours or shorter, 2 hours or shorter, 110 minutes or shorter, 100 minutes or shorter. The enzyme treatment temperature is not particularly limited and is, for example, 15° C. or higher, 16° C. or higher, 17° C. or higher, 18° C. or higher, 19° C. or higher, 20° C. or higher, 21° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher or 36° C. or higher. Also, the enzyme treatment temperature is not particularly limited and is, for example, 40° C. or lower, 39° C. or lower, 38° C. or lower or 37° C. or lower.

In the production method of the present invention, if desired, the released mesenchymal stem cells can be separated and/or recovered from the enzyme solution containing the released mesenchymal stem cells by a known method such as a filter, centrifugation, a hollow fiber separation membrane, or a cell sorter. Preferably, the enzyme solution containing the released mesenchymal stem cells is filtered through a filter. In an aspect of filtering the enzyme solution through a filter, only the released cells pass through the filter, whereas an undegraded epithelial cell layer remains on the filter without passing through the filter. Therefore, not only can the released mesenchymal stem cells be easily separated and/or recovered, but the risk of contamination by bacteria, viruses, and the like can be reduced. Examples of the filter can include, but are not particularly limited to, mesh filters. The pore size (mesh size) of the mesh filter is not particularly limited and is, for example, 40 μm or larger, 50 μm or larger, 60 μm or larger, 70 μm or larger, 80 μm or larger, or 90 μm or larger. Also, the pore size of the mesh filter is not particularly limited and is, for example, 200 μm or smaller, 190 μm or smaller, 180 μm or smaller, 170 μm or smaller, 160 μm or smaller, 150 μm or smaller, 140 μm or smaller, 130 μm or smaller, 120 μm or smaller, 110 μm or smaller, or 100 μm or smaller. The filtration rate is not particularly limited. When the pore size of the mesh filter falls within the range described above, the enzyme solution containing the mesenchymal stem cells can be filtered by free fall. This can prevent decrease in cell survival rate.

Nylon is preferably used as a material for the mesh filter. A tube containing a 40 μm, 70 μm, 95 μm or 100 μm nylon mesh filter such as a Falcon cell strainer, which is widely used for research purposes, is available. Alternatively, medical mesh cloth (nylon and polyester) used for hemodialysis and the like is available. Further, an arterial filter used for extracorporeal circulation (polyester mesh filter, pore size: 40 μm or larger and 120 μm or smaller) is also available. A mesh made of any other material, for example, a stainless-steel mesh filter, may be used.

Preferably, the mesenchymal stem cells are allowed to pass through a filter in a free fall motion. It is also possible to force the cells to pass through a filter by suction using a pump or the like. In this case, in order to avoid damage of the cells, minimum necessary pressurization is desirable.

The mesenchymal stem cells that have passed through the filter can be recovered by centrifugation after dilution of the filtrate with two times or more its volume of a medium or balanced salt buffer solution. Examples of the balanced salt buffer solution that can be used include, but are not limited to, Dulbecco's phosphate-buffered saline (DPBS), Earle's balanced salt solution (EBSS), Hank's balanced salt solution (HBSS), and phosphate-buffered saline (PBS).

The cell population obtained in the cell population obtainment step is cultured under conditions that maintain the proportion of CD105$^+$ mesenchymal stem cells in the cell population which is 50% or more, the proportion of CD200$^+$ mesenchymal stem cells in the cell population which is less than 10%, and the proportion of CD106$^+$ mesenchymal stem cells in the cell population which is less than 5%. The conditions are useful as an index for obtaining a cell population comprising highly proliferative mesenchymal stem cells. The culture method is not particularly limited as long as the index is satisfied. Examples of such a method can include a step of repeating a plurality of times the seeding of the cell population comprising cells collected from the fetal appendage at a density of 400 to 5,000 cells/cm$^2$, followed by culture. The density of the cell population for seeding is more preferably 500 cells/cm$^2$ or more, further preferably 600 cells/cm² or more, further preferably 700 cells/cm² or more, further preferably 800 cells/cm² or more, further preferably 900 cells/cm² or more, further preferably 1000 cells/cm² or more, further preferably 1100 cells/cm² or more, further preferably 1200 cells/cm² or more, further preferably 1300 cells/cm² or more, further preferably 1400 cells/cm² or more, further preferably 1500 cells/cm² or more, further preferably 1600 cells/cm² or more, further preferably 1700 cells/cm² or more, further preferably 1800 cells/cm² or more, further preferably 1900 cells/cm² or more, and further preferably 2000 cells/cm² or more. The density of the cell population for seeding is more preferably 4800 cells/cm² or less, further preferably 4600 cells/cm² or less, further preferably 4400 cells/cm² or less, further preferably 4200 cells/cm² or less, further preferably 4000 cells/cm² or less, further preferably 3800 cells/cm² or less, further preferably 3600 cells/cm² or less, further preferably 3400 cells/cm² or less, further preferably 3200 cells/cm² or less, further preferably 3000 cells/cm² or less, further preferably 2800 cells/cm² or less, further preferably 2600 cells/cm² or less, further preferably 2400 cells/cm² or less, and further preferably 2200 cells/cm² or less.

Examples of the culture period of time of one culture process can include 4 to 10 days and can more specifically include 4 days, 5 days, 6 days, 7 days, 8 days, 9 days and 10 days.

The medium for use in the culture can be prepared by utilizing any liquid medium for animal cell culture as a basal medium and, if necessary, appropriately adding thereto other components (serum, a serum replacement reagent, a growth factor, etc.). In an aspect of adding a growth factor to the basal medium, the medium may be prepared by adding a reagent (heparin, etc.) for stabilizing the growth factor in the medium, to the growth factor, and further adding the mixture to the basal medium, or may be prepared by stabilizing the growth factor in advance with a gel, a polysaccharide, or the like, and then adding the stabilized growth factor to the basal medium.

Examples of the basal medium that can be used include, but are not particularly limited to, media such as BME medium, BGJb medium, CMRL1066 medium, Glasgow MEM medium, improved MEM zinc option medium, IMDM medium (Iscove's modified Dulbecco's medium), Medium 199 medium, Eagle MEM medium, αMEM (alpha modification of minimum essential medium eagle) medium, DMEM medium (Dulbecco's modified Eagle's medium), Ham's F10 medium, Hams' F12 medium, RPMI 1640 medium, Fischer's medium, and mixed media thereof (e.g., DMEM/F12 medium (Dulbecco's modified Eagle's medium/nutrient mixture F-12 Ham)).

Examples of other components include albumin, serum, serum replacement reagents and growth factors. In the case of albumin, its concentration is preferably higher than 0.05% and 5% or lower. In the case of serum, its concentration is preferably 5% or higher.

Alternatively, the medium for use in the culture may be a commercially available serum-free medium. Examples thereof include, but are not particularly limited to, STK1 and STK2 (DS Pharma Biomedical Co., Ltd.), EXPREP MSC Medium (BioMimetics Sympathies Inc.), and Corning stemgro human mesenchymal stem cell medium (Corning Inc.).

The culture of mesenchymal stem cells can be performed by, for example, the following process: first, a cell suspension is centrifuged. The supernatant is removed, and the obtained cell pellet is suspended in a medium. Next, the cells are seeded to a plastic culture vessel and cultured using a medium in an environment of a $CO_2$ concentration of 3% or higher and 5% or lower at 37° C. until 95% or less confluence. Examples of the medium can include, but are not limited to, αMEM, M199, and media based thereon. The cells obtained by the culture as described above are cells cultured once.

The cells cultured once can be further passaged and cultured, for example, as follows: first, the cells cultured once are dissociated from the plastic culture vessel by treatment with ethylenediaminetetraacetic acid (EDTA) followed by treatment with trypsin. Next, the obtained cell suspension is centrifuged. The supernatant is removed, and the obtained cell pellet is suspended in a medium. Finally, the cells are seeded to a plastic culture vessel and cultured using a medium in an environment of a $CO_2$ concentration of 3% or higher and 5% or lower at 37° C. until 95% or less confluence. Examples of the medium can include, but are not limited to, αMEM, M199, and media based thereon. The cells obtained by the passage and the culture as described above are cells passaged once. Cells passaged N times can be obtained by similar passage and culture (N represents an integer of 1 or more). The lower limit of passage number N is, for example, 1 or more, preferably 2 or more, more preferably 3 or more, further preferably 4 or more, further preferably 5 or more, further preferably 6 or more, further preferably 7 or more, further preferably 8 or more, further preferably 9 or more, further preferably 10 or more, further preferably 11 or more, further preferably 12 or more, further preferably 13 or more, further preferably 14 or more, further preferably 15 or more, further preferably 16 or more, further preferably 17 or more, further preferably 18 or more, further preferably 19 or more, further preferably 20 or more, and further preferably 25 or more, from the viewpoint of producing the cells at a large scale. Also, the upper limit of passage number N is, for example, preferably 50 or less, 45 or less, 40 or less, 35 or less, or 30 or less, from the viewpoint of suppressing cell senescence.

According to the production method of the present invention, mesenchymal stem cells having high proliferative capacity can be obtained. This enables large-scale and rapid production of a cell preparation (pharmaceutical composition). The lower limit of the obtained cell count per batch of culture (cell count obtained per unit surface area and per unit number of culture days) differs depending on a seeded cell count, a seeding density, etc. and is, for example, $1.0 \times 10^5$ (cells/cm²/day) or more, $2.0 \times 10^5$ (cells/cm²/day) or more, $3.0 \times 10^5$ (cells/cm²/day) or more, $4.0 \times 10^5$ (cells/cm²/day) or more, $5.0 \times 10^5$ (cells/cm²/day) or more, $6.0 \times 10^5$ (cells/cm²/day) or more, $7.0 \times 10^5$ (cells/cm²/day) or more, $8.0 \times 10^5$ (cells/cm²/day) or more, $9.0 \times 10^5$ (cells/cm²/day) or more or $10.0 \times 10^5$ (cells/cm²/day) or more. Also, the upper limit of the obtained cell count per batch of culture is not particularly limited and is, for example, $10.0 \times 10^8$ (cells/cm²/day) or less, $9.0 \times 10^8$ (cells/cm²/day) or less, $8.0 \times 10^8$ (cells/cm²/day) or less, $7.0 \times 10^8$ (cells/cm²/day) or less, $6.0 \times 10^8$ (cells/cm²/day) or less, $5.0 \times 10^8$ (cells/cm²/day) or less, $4.0 \times 10^8$ (cells/cm²/day) or less, $3.0 \times 10^8$ (cells/cm²/day) or less, $2.0 \times 10^8$ (cells/cm²/day) or less or $1.0 \times 10^8$ (cells/cm²/day) or less.

According to the production method of the present invention, mesenchymal stem cells having high proliferative capacity can be obtained. The mesenchymal stem cells obtained by the production method of the present invention are thereby culturable without the arrest of proliferation preferably up to 40 days or later, and more preferably up to 45 days or later, up to 50 days or later, up to 55 days or later, up to 60 days or later, up to 65 days or later, up to 70 days or later, up to 75 days or later, up to 80 days or later, up to 85 days or later, up to 90 days or later, up to 95 days or later, up to 100 days or later, up to 105 days or later, or up to 110 days or later, after the start of ex vivo culture.

The mesenchymal stem cells obtained by the production method of the present invention are also culturable up to a population doubling level of preferably 10 or more, and more preferably 15 or more, 20 or more, 25 or more, 30 or more, 35 or more, 40 or more, 45 or more, or 50 or more, after the start of ex vivo culture.

The production method of the present invention may comprise an identification step of identifying a population comprising highly proliferative mesenchymal stem cells by utilizing, as an index, the proportion of CD105$^+$ mesenchymal stem cells in the cell population comprising mesenchymal stem cells which is 50% or more, the proportion of CD200$^+$ mesenchymal stem cells in the cell population which is less than 10%, and the proportion of CD106$^+$ mesenchymal stem cells in the cell population which is less than 5%.

The production method of the present invention can also comprise a step of cryopreserving the cell population comprising mesenchymal stem cells. In an aspect comprising a step of cryopreserving the cell population, the cell population may be thawed, and then, if necessary, separated, recovered and/or cultured. Alternatively, the cell population may be thawed and then directly used.

Examples of the means for cryopreserving the cell population comprising mesenchymal stem cells include, but are not particularly limited to, programmable freezers, deep freezers, and dipping in liquid nitrogen. The temperature for freezing is preferably −30° C. or lower, −40° C. or lower, −50° C. or lower, −60° C. or lower, −70° C. or lower, −80° C. or lower, −90° C. or lower, −100° C. or lower, −110° C. or lower, −120° C. or lower, −130° C. or lower, −140° C. or lower, −150° C. or lower, −160° C. or lower, −170° C. or lower, −180° C. or lower, −190° C. or lower, or −196° C. (liquid nitrogen temperature) or lower. The freezing rate for freezing is, for example, preferably −1° C./min, −2° C./min, −3° C./min, −4° C./min, −5° C./min, −6° C./min, −7° C./min, −8° C./min, −9° C./min, −10° C./min, −11° C./min, −12° C./min, −13° C./min, −14° C./min or −15° C./min. In the case of using a programmable freezer as such freezing means, the temperature can be lowered to a temperature between −50° C. or higher and −30° C. or lower (e.g., −40° C.) at a freezing rate of, for example, −2° C./min or more and −1° C./min or less, and further lowered to a temperature of −100° C. or higher and −80° C. or lower (e.g., −90° C.) at a freezing rate of −11° C./min or more and −9° C./min or less (e.g., −10° C./min).

For freezing by the freezing means, the cell population may be frozen in a state contained in an any preservation container. Examples of such a preservation container include, but are not limited to, cryotubes, cryovials, bags for freezing, and infusion bags.

The cryopreservation solution preferably contains albumin at a predetermined concentration larger than 0% by mass from the viewpoint of enhancing the survival rate of MSCs having relatively high proliferative capacity. The concentration of the albumin is, for example, preferably 0.5% by mass or higher, 1% by mass or higher, 2% by mass or higher, 3% by mass or higher, 4% by mass or higher, 5% by mass or higher, 6% by mass or higher, 7% by mass or higher or 8% by mass or higher. Also, the concentration of the albumin is, for example, preferably 40% by mass or lower, 35% by mass or lower, 30% by mass or lower, 25% by mass or lower, 20% by mass or lower, 15% by mass or lower, 10% by mass or lower or 9% by mass or lower. Examples of the albumin can include, but are not limited to, bovine serum albumin, mouse albumin, and human albumin.

[4] Method for Monitoring Proliferative Properties of Mesenchymal Stem Cells, Method for Evaluating Donor and/or Sample Collected from the Donor, and Method for Confirming and/or Predicting Enzyme Treatment Conditions In the present invention, the proliferative properties of mesenchymal stem cells can be monitored by measuring, as an index, the proportion of CD105$^+$ mesenchymal stem cells which is 50% or more in a cell population comprising mesenchymal stem cells, the proportion of CD200$^+$ mesenchymal stem cells in the cell population which is less than 10%, and the proportion of CD106$^+$ mesenchymal stem cells in the cell population which is less than 5% (preferably over time). Examples of the step that requires the monitoring include a culture step, a cryopreservation step, and/or a formulation step.

In the culture step, changes in the proliferative properties of mesenchymal stem cells can be rapidly grasped and predicted by measuring the index over time. In a cell population comprising mesenchymal stem cells that satisfy the index, the mesenchymal stem cells are found to be highly proliferative. On the other hand, when a culture state continues with a value deviating from the index, it can be predicted that the proliferative properties of mesenchymal stem cells are being reduced. For example, in the cell population comprising mesenchymal stem cells that satisfy the index, the population doubling time is kept equal to or less than a given numeric value. On the other hand, when a culture state continues with a value deviating from the index, data on the population doubling time exceeding the given numeric value is obtained. When the index teaches that the proliferative properties are being reduced, the proliferative properties of mesenchymal stem cells can be improved by properly changing culture conditions (a seeding density, a medium, the addition of a growth factor, change of serum, etc.) according to the need. When the index is not satisfied, a cell population comprising mesenchymal stem cells that satisfy the index can be separated through the use of, for example, a cell sorting technique. The mesenchymal stem cells in the cell population can be seeded again and subcultured to improve the proliferative properties of the mesenchymal stem cells. At the early stage of culture, culture conditions (a seeding density, a medium, the addition of a growth factor, change of serum, etc.) are designed such that the index is satisfied at the final stage of the step. Thus, the index can be satisfied at least at the final stage.

In the present invention, the quality of a donor itself and/or a sample collected from the donor can be evaluated by obtaining a cell population comprising mesenchymal stem cells derived from the fetal appendage from the donor, measuring the proportion of CD105$^+$ mesenchymal stem cells, the proportion of CD200$^+$ mesenchymal stem cells and the proportion of CD106$^+$ mesenchymal stem cells, and making evaluation by utilizing, as an index, the proportion of CD105$^+$ mesenchymal stem cells in the cell population which is 50% or more, the proportion of CD200$^+$ mesenchymal stem cells in the cell population which is less than 10%, and the proportion of CD106$^+$ mesenchymal stem cells in the cell population which is less than 5%. When a cell population comprising mesenchymal stem cells that satisfy the index is obtained (preferably, easily obtained), the quality of the donor and/or the sample collected from the donor can be confirmed to be good. On the other hand, when the proportions in the cell population comprising mesenchymal stem cells deviate from the index, the quality of the sample collected from the donor is poor. Therefore, the proliferative properties of mesenchymal stem cells can be improved by properly changing culture conditions (a seeding density, a medium, the addition of a growth factor, change of serum, etc.). When the proportions in the cell population comprising mesenchymal stem cells deviate from the index, a cell population comprising mesenchymal stem cells that satisfy the index can be separated through the use of, for example, a cell sorting technique. The mesenchymal stem cells in the cell population can be seeded and cultured to improve the proliferative properties of the mesenchymal stem cells. At the early stage of culture, culture conditions (a seeding density, a medium, the addition of a growth factor, change of serum, etc.) are designed such that the index is satisfied at the final stage of the step. Thus, the index can be satisfied at least at the final stage. In the case of confirming the quality of the sample collected from the donor, methods for preparing and treating the sample, and a method for culturing the cell population are not particularly limited, and any methods can be adopted.

In the present invention, enzyme treatment conditions optimum for a sample collected from a donor can be determined and/or predicted by measuring the proportion of $CD105^+$ mesenchymal stem cells, the proportion of $CD200^+$ mesenchymal stem cells and the proportion of $CD106^+$ mesenchymal stem cells in a cell population obtained by the enzyme treatment of the sample, and making evaluation by utilizing, as an index, the proportion of $CD105^+$ mesenchymal stem cells in the cell population which is 50% or more, the proportion of $CD200^+$ mesenchymal stem cells in the cell population which is less than 10%, and the proportion of $CD106^+$ mesenchymal stem cells in the cell population which is less than 5%. When a cell population comprising mesenchymal stem cells that satisfy the index is obtained (preferably, easily obtained), the enzyme treatment method can be determined and/or predicted to be proper for the sample collected from a donor. On the other hand, when a culture state continues with a value deviating from the index, the enzyme treatment method can be determined and/or predicted to be not proper for the sample collected from a donor. In the case of determining and/or predicting an optimum enzyme treatment method, methods for preparing and treating the sample, and a method for culturing the cell population are not particularly limited, and any methods can be adopted.

The index can be measured at a necessary timing. Examples of the timing include, but are not particularly limited to, immediately after separation of cells from a biological sample, during the course of a culture step, after purification in the culture step, immediately after the Nth passage (N represents an integer of 1 or more), during the course of maintenance culture, before cryopreservation, after thawing, and before formulation as a pharmaceutical composition.

[5] Pharmaceutical Composition

The cell population comprising mesenchymal stem cells derived from the fetal appendage according to the present invention can be used as a pharmaceutical composition. Specifically, the present invention provides a pharmaceutical composition comprising the cell population comprising mesenchymal stem cells derived from the fetal appendage according to the present invention, and a pharmaceutically acceptable carrier.

The pharmaceutical composition of the present invention can be used as a cell therapy agent, for example, a therapeutic agent for intractable diseases.

The pharmaceutical composition of the present invention can be used as a therapeutic agent for a disease selected from immunological diseases, ischemic diseases (lower-limb ischemia, ischemic heart disease (myocardial infarction, etc.), coronary heart disease, cerebrovascular ischemia, renal ischemia, pulmonary ischemia, etc.), neurological diseases, graft-versus-host disease (GVHD), inflammatory bowel diseases including Crohn's disease and ulcerative colitis, collagen diseases including systemic lupus erythematosus, cerebral infarction, intracerebral hematoma, vasoparalysis, radiation enteritis, liver cirrhosis, stroke, atopic dermatitis, multiple sclerosis, rheumatoid arthritis, psoriasis, lupus erythematosus, diabetes mellitus, mycosis fungoides (Alibert-Bazin syndrome), scleroderma, diseases caused by the degeneration and/or inflammation of connective tissues such as cartilage, eye diseases, angiogenesis-related diseases, congestive heart failure, cardiomyopathy, wounds, epithelial damage, fibrosis, lung diseases, cancers, and the like. The pharmaceutical composition of the present invention can be administered in a measurably effective amount to a treatment site to thereby treat the disease.

The present invention provides the cell population comprising mesenchymal stem cells derived from the fetal appendage according to the present invention for use in a pharmaceutical composition.

The present invention provides the cell population comprising mesenchymal stem cells derived from the fetal appendage according to the present invention for use in a cell therapy agent.

The present invention provides the cell population comprising mesenchymal stem cells derived from the fetal appendage according to the present invention for use in the treatment of a disease selected from immunological diseases, ischemic diseases (lower-limb ischemia, ischemic heart disease (myocardial infarction, etc.), coronary heart disease, cerebrovascular ischemia, renal ischemia, pulmonary ischemia, etc.), neurological diseases, graft-versus-host disease (GVHD), inflammatory bowel diseases including Crohn's disease and ulcerative colitis, collagen diseases including systemic lupus erythematosus, cerebral infarction, intracerebral hematoma, vasoparalysis, radiation enteritis, liver cirrhosis, stroke, atopic dermatitis, multiple sclerosis, rheumatoid arthritis, psoriasis, lupus erythematosus, diabetes mellitus, mycosis fungoides (Alibert-Bazin syndrome), scleroderma, diseases caused by the degeneration and/or inflammation of connective tissues such as cartilage, eye diseases, angiogenesis-related diseases, congestive heart failure, cardiomyopathy, wounds, epithelial damage, fibrosis, lung diseases, cancers, and the like.

The present invention provides the cell population comprising mesenchymal stem cells derived from the fetal appendage according to the present invention for use in the regeneration of cardiac muscle, the production of cardiac muscle cells, angiogenesis, the repair of a blood vessel, or the suppression of immune response by administration to a patient or a subject.

The present invention provides a method for transplanting cells to a patient or a subject, and a method for treating a disease in a patient or a subject, comprising a step of administering a therapeutically effective amount of the cell population comprising mesenchymal stem cells derived from the fetal appendage according to the present invention to the patient or the subject.

The present invention provides use of the cell population comprising mesenchymal stem cells derived from the fetal appendage according to the present invention for the production of a pharmaceutical composition.

The present invention provides use of the cell population comprising mesenchymal stem cells derived from the fetal appendage according to the present invention for the production of a cell therapy agent.

The present invention provides use of the cell population comprising mesenchymal stem cells derived from the fetal appendage according to the present invention for the production of a therapeutic agent for a disease selected from immunological diseases, ischemic diseases (lower-limb ischemia, ischemic heart disease (myocardial infarction, etc.), coronary heart disease, cerebrovascular ischemia, renal ischemia, pulmonary ischemia, etc.), neurological diseases, graft-versus-host disease (GVHD), inflammatory bowel diseases including Crohn's disease and ulcerative colitis, collagen diseases including systemic lupus erythematosus, cerebral infarction, intracerebral hematoma, vasoparalysis, radiation enteritis, liver cirrhosis, stroke, atopic dermatitis, multiple sclerosis, rheumatoid arthritis, psoriasis, lupus erythematosus, diabetes mellitus, mycosis fungoides (Alibert-Bazin syndrome), scleroderma, diseases caused by the degeneration and/or inflammation of connective tissues such as cartilage, eye diseases, angiogenesis-related diseases, congestive heart failure, cardiomyopathy, wounds, epithelial damage, fibrosis, lung diseases, cancers, and the like.

The present invention provides use of the cell population comprising mesenchymal stem cells derived from the fetal appendage according to the present invention for the production of a therapeutic agent necessary for the regeneration of cardiac muscle, the production of cardiac muscle cells, angiogenesis, the repair of a blood vessel, or the suppression of immune response by administration to a patient or a subject.

The dose of the pharmaceutical composition of the present invention is the amount of cells that allows a patient or a subject to whom the pharmaceutical composition has been administered to obtain therapeutic effects, compared with a patient or a subject to whom the pharmaceutical composition has not been administered. A specific dose can be appropriately determined depending on the form of administration, an administration method, intended use, and patient's or subject's age, body weight, and symptoms, and the like. The dose is not particularly limited and is, for example, $10^4$ cells/kg body weight or more, $10^5$ cells/kg body weight or more or $10^6$ cells/kg body weight or more. Also, the dose is not particularly limited and is, for example, $10^9$ cells/kg body weight or less, $10^8$ cells/kg body weight or less or $10^7$ cells/kg body weight or less.

Examples of the method for administering the pharmaceutical composition of the present invention include, but are not particularly limited to, subcutaneous injection, intralymph nodal injection, intravenous injection, intraperitoneal injection, intrathoracic injection, direct localized injection, and direct localized transplantation.

The pharmaceutical composition of the present invention may be used as an injection preparation, a transplant preparation having a cell aggregate or sheet-like structure, or a gel preparation mixed with any gel, for the purpose of treating other diseases.

The patient or the subject of the present invention is typically a human and may be other animals. Examples of other animals include mammal such as dogs, cats, cattle, horses, pigs, sheep, monkeys, and ferrets, and birds such as chickens.

The pharmaceutical composition of the present invention can be preserved in a frozen state until immediately before use. The pharmaceutical composition of the present invention may comprise any component for use in the treatment of humans. Examples of such a component can include, but are not limited to, salts, polysaccharides (e.g., HES and dextran), proteins (e.g., albumin), DMSO, and medium components (e.g., components contained in RPMI1640 medium).

The pharmaceutical composition of the present invention may be an amniotic mesenchymal stem cell population diluted with an infusion preparation for use as a pharmaceutically acceptable carrier. The term "infusion preparation (pharmaceutically acceptable carrier)" used herein is not particularly limited as long as it is a solution for use in the treatment of humans. Examples thereof include physiological saline, 5% glucose solution, Ringer's solution, lactated Ringer's solution, acetated Ringer's solution, starter solution (Solution I), rehydration solution (Solution II), maintenance infusion (Solution III), and postoperative recovery solution (Solution IV).

For other examples of diseases, etc. that can be treated using the cell population comprising mesenchymal stem cells in the patient or the subject, further specific examples of the diseases, etc., and specific procedures of treatment, see items described in Hare et al., J. Am. Coll. Cardiol., 2009 Dec. 8; 54 (24): 2277-2286, Honmou et al., Brain 2011: 134; 1790-1807, Makhoul et al., Ann. Thorac. Surg. 2013; 95: 1827-1833, JP Patent No. 590577, JP Patent Publication (Kokai) No. 2010-518096 A (2010), JP Patent Publication (Kohyo) No. 2012-509087 A (2012), JP Patent Publication (Kohyo) No. 2014-501249 A (2014), JP Patent Publication (Kokai) No. 2013-256515 A (2013), JP Patent Publication (Kokai) No. 2014-185173 A (2014), JP Patent Publication (Kohyo) No. 2010-535715 A (2010), JP Patent Publication (Kokai) No. 2015-038059 A (2015), JP Patent Publication (Kokai) No. 2015-110659 A (2015), JP Patent Publication (Kohyo) No. 2006-521121 A (2006), JP Patent Publication (Kohyo) No. 2009-542727 A (2009), JP Patent Publication (Kokai) No. 2014-224117 A (2014), JP Patent Publication (Kokai) No. 2015-061862 A (2015), JP Patent Publication (Kohyo) No. 2002-511094 A (2002), JP Patent Publication (Kohyo) No. 2004-507454 A (2004), JP Patent Publication (Kohyo) No. 2010-505764 A (2010), JP Patent Publication (Kohyo) No. 2011-514901 A (2011), JP Patent Publication (Kokai) No. 2013-064003 A (2013), JP Patent Publication (Kokai) No. 2015-131795 A (2015), etc.

The present invention is specifically explained with reference to the Examples below; however, the present invention is not limited to the Examples.

EXAMPLES

Comparative Example 1

(Step 1-1: Collection of Amnion)

A fetal membrane and a placenta were aseptically collected as the fetal appendage from a pregnant woman who was an elective cesarean section case after the obtaining of informed consent. The obtained fetal membrane and placenta were contained in a sterile tray containing physiological saline. An amnion was manually separated from the stump of the fetal membrane. The amnion was washed with a Hank's balanced salt solution (free of Ca and Mg) to remove attached blood and clots.

(Step 1-2: Enzyme Treatment of Amnion and Recovery of Amniotic MSCs)

The amnion comprising an epithelial cell layer and a mesenchymal stem cell layer was dipped in a Hank's balanced salt solution (containing Ca and Mg) containing 480 PU/mL collagenase and 400 PU/mL dispase I. The amnion was enzyme-treated by shaking and stirring under conditions of 37° C., 90 minutes, and 50 rpm. The solution thus enzyme-treated was filtered through a nylon mesh having openings of 95 μm for the removal of undigested products of the amnion to recover a cell suspension containing amniotic MSCs. The obtained cell suspension was analyzed for the proportion of cells positive for the expression of CD90, a surface antigen known as a typical positive marker of MSCs, using a flow cytometer. As a result, the proportion of cells positive for the expression of CD90 was 89%, confirming that amniotic MSCs were able to be separated with high purity from the amnion.

The surface antigen analysis employed BD Accuri™ C6 Flow Cytometer from Becton, Dickinson and Company, and the measurement conditions involved analyzed cell count: 10,000 cells and flow rate setting: Slow (14 μL/min). The antibody for isotype control used was FITC Mouse IgG1, κ Isotype Control (Becton, Dickinson and Company/model number: 550616). The antibody against the CD90 antigen used was FITC Mouse Anti-Human CD90 (Becton, Dickinson and Company/model number: 555595). The proportion of cells positive for the CD90 antigen was calculated by the following procedures.

(1) The measurement results were plotted as a histogram with a cell count on the ordinate against the fluorescence intensity of a dye of the labeled antibody on the abscissa.
(2) The fluorescence intensity at which 0.1 to 1.0% cell population exhibited stronger fluorescence intensity among all cells measured with the antibody for isotype control was determined.
(3) The percentage of cells having stronger fluorescence intensity than that determined in (2) among all cells measured with the antibody against the CD90 antigen was calculated.

(Step 1-3: Culture of Amniotic MSCs; Usual Culture)

The cell population comprising the amniotic MSCs obtained in the above section "Enzyme treatment of amnion and recovery of amniotic MSCs" was seeded at a density of 4,000 cells/cm² to a plastic culture vessel and cultured until subconfluent in αMEM (alpha modification of minimum essential medium Eagle) containing 10% fetal bovine serum (FBS). Then, the cells were dissociated using TrypLE Select. A ¼ amount of the cells was seeded to a plastic culture vessel at the same scale as that of the preceding culture and thereby subcultured. Medium replacement was carried out with a frequency of twice a week. As a result of continuing subculture in this way, the cells were able to be passaged up to 4 times. However, after the completion of the 4th passage, the proliferation of the amniotic MSCs was arrested. As a result of observing cell morphology, the cells up to the 2nd passage were fusiform, whereas the cells of the 3rd or later passage were flattened (FIG. 1).

From the cell morphology, the amniotic MSCs in this culture presumably fell into a poor culture state from the stage of the 3rd passage. The amniotic MSCs of each passage obtained by this subculture were evaluated for the positive rates of various surface antigens (CD73, CD90, and CD105) using a flow cytometer (FIG. 2). P0, P1, P2, P3 and P4 mean cells of passage number 0, passage number 1, passage number 2, passage number 3 and passage number 4, respectively. In this assay, the antibodies for isotype control used were PE Mouse IgG1, κ Isotype Control (Becton, Dickinson and Company/model number: 555749) and FITC Mouse IgG1, κ Isotype Control (Becton, Dickinson and Company/model number: 550616). The antibody against the CD73 antigen used was PE Mouse Anti-Human CD73 (Becton, Dickinson and Company/model number: 550257). The antibody against the CD90 antigen used was FITC Mouse Anti-Human CD90 (Becton, Dickinson and Company/model number: 555595). The antibody against the CD105 antigen used was Anti-Human Antibodies FITC Conjugate (Ancell Corp./model number: 326-040). The measurement of cells and the calculation of the proportions of positive cells were performed by the same procedures as in the above section "Enzyme treatment of amnion and recovery of amniotic MSCs". As a result, the proportions of cells positive for these surface antigens were high at the 2nd passage, whereas the proportions of positive cells were decreased at the 3rd or later passage. This demonstrated that decrease in the positive rates of CD73, CD90, and CD105 sharply reduces the proliferative properties of mesenchymal stem cells, resulting in a poor culture state. Thus, the positive rates of surface antigens such as CD73, CD90, and CD105 can be utilized as an index for evaluating the proliferative properties of mesenchymal stem cells. Also, a population doubling level was calculated on a passage basis to prepare a growth curve (usual culture in FIG. 6).

Example 1: Culture of Amniotic MSCs (Culture According to Present Invention)

The cell population comprising the amniotic MSCs obtained in the above "Step 1-2: Enzyme treatment of amnion and recovery of amniotic MSCs" was seeded at a density of 2,000 cells/cm² to a plastic culture vessel and cultured for 1 week in αMEM (alpha modification of minimum essential medium Eagle) containing 10% fetal bovine serum (FBS). Medium replacement was carried out with a frequency of twice a week. Then, subculture involving seeding at a density of 2,000 cells/cm² was similarly repeated. As a result, the percentage of fusiform and small-sized cells was increased as the passage was repeated, and a large number of cells were fusiform and small-sized at the stage of the 4th passage (FIG. 7).

The cells obtained at this stage were used to repeat subculture involving a passage at the same density as above in αMEM (alpha modification of minimum essential medium Eagle) containing 10% fetal bovine serum (FBS).

The amniotic MSCs of the 7th, 9th, and 11th passages cultured by the culture method described above were analyzed for the proportions of cells positive for various surface antigens (CD73, CD90, CD105, CD14, CD45, CD106, and CD200 known as amniotic MSC markers) using a flow cytometer (7th passage: bFGF(-) in FIG. 3, 9th passage: bFGF(-) in FIG. 4, 11th passage: bFGF(-) in FIG. 5). As a result, the positive rate of CD105 was 50% or more (specifically, 7th passage: 98%, 9th passage: 88%, 11th passage: 73%), the positive rate of CD200 was less than 10% (specifically, 7th passage: 4%, 9th passage: 6%, 11th passage: 5%), the positive rate of CD14 was 5% or more (specifically, 7th passage: 8%, 9th passage: 16%, 11th passage: 18%), and the positive rate of CD106 was less than 5% (specifically, 7th passage: 0%, 9th passage: 4%, 11th passage: 4%). Thus, the cell population comprising the fetal appendage-derived mesenchymal stem cells obtained by the method of the present invention was found to have mesenchymal stem cells positive for the monocyte marker CD14 and to have only a very small amount of mesenchymal stem cells positive for the fetal-specific marker CD200.

In this assay, the antibodies for isotype control used were PE Mouse IgG1, κ Isotype Control (Becton, Dickinson and Company/model number: 555749), FITC Mouse IgG1, κ Isotype Control (Becton, Dickinson and Company/model number: 550616), and FITC Mouse IgG2a, κ Isotype Control, REA Control (S)-PE isotype control antibody (Miltenyi Biotec/130-104-612). The antibody against the CD73 antigen used was PE Mouse Anti-Human CD73 (Becton, Dickinson and Company/model number: 550257). The antibody against the CD90 antigen used was FITC Mouse Anti-Human CD90 (Becton, Dickinson and Company/model number: 555595). The antibody against the CD105 antigen used was Anti-Human Antibodies FITC Conjugate (Ancell Corp./model number: 326-040). The antibody against the CD14 antigen used was FITC Mouse Anti-Human CD14 (Becton, Dickinson and Company/model number: 555397). The antibody against the CD45 antigen used was FITC Mouse Anti-Human CD45 (Becton, Dickinson and Company/model number: 555482). The antibody against the CD200 antigen used was PE Mouse Anti-Human CD200 (Becton, Dickinson and Company/model number: 561762). The antibody against the CD106 antigen used was CD106-PE, human monoclonal (Miltenyi Biotec/130-104-163).

The measurement of cells and the calculation of the proportions of positive cells were performed by the same procedures as in the above "Step 1-2; Enzyme treatment of amnion and recovery of amniotic MSCs"

The culture of the amniotic MSCs of the 11th passage was further continued by the culture method described above. As a result, the amniotic MSCs were culturable without the arrest of proliferation at least up to 107 days as the total number of culture days and a population doubling level of 46. A growth curve was also prepared as to the amniotic MSCs thus cultured in the same way as in "Step 1-3; Culture of amniotic MSCs; usual culture" (culture of the present invention (bFGF−) in FIG. 6). The population doubling time at the 7th passage was 1.6 days, the population doubling time at the 9th passage was 1.5 days, and the population doubling time at the 11th passage was 1.3 days.

These results demonstrated that amniotic MSCs that satisfy conditions involving the positive rate of CD105 which is 50% or more, the positive rate of CD200 which is less than 10%, the positive rate of CD14 which is 5% or more, and the positive rate of CD106 which is less than 5% are highly proliferative and also have a population doubling time of 2 days or shorter.

Example 2: Culture of Amniotic MSCs (Addition of Basic Fibroblast Growth Factor (bFGF))

The cell population comprising the amniotic MSCs obtained in the above "Step 1-2: Enzyme treatment of amnion and recovery of amniotic MSCs" was seeded at a density of 2,000 cells/cm$^2$ to a plastic culture vessel and cultured for 1 week in αMEM (alpha modification of minimum essential medium Eagle) containing 10% fetal bovine serum (FBS). Medium replacement was carried out with a frequency of twice a week. Then, subculture involving seeding at a density of 2,000 cells/cm$^2$ was similarly repeated. As a result, the percentage of fusiform and small-sized cells was increased as the passage was repeated, and a large number of cells were fusiform and small-sized at the stage of the 4th passage.

The cells obtained at this stage were used to repeat subculture involving a passage at the same density as above in αMEM (alpha modification of minimum essential medium Eagle) containing 10% fetal bovine serum (FBS) and 10 ng/mL basic fibroblast growth factor (bFGF) (both in terms of final concentration).

The amniotic MSCs of the 7th, 9th, and 11th passages cultured by the culture method described above were analyzed for the proportions of cells positive for various surface antigens (CD73, CD90, CD105, CD14, CD45, CD106, and CD200 known as amniotic MSC markers) using a flow cytometer (7th passage: bFGF(+) in FIG. 3, 9th passage: bFGF(+) in FIG. 4, 11th passage: bFGF(+) in FIG. 5). As a result, the positive rate of CD105 was 50% or more (specifically, 7th passage: 79%, 9th passage: 86%, 11th passage: 87%), the positive rate of CD200 was less than 10% (specifically, 7th, 9th, and 11th passages: all 0%), the positive rate of CD14 was 5% or more (specifically, 7th passage: 12%, 9th passage: 8%, 11th passage: 8%), and the positive rate of CD106 was less than 5% (specifically, 7th, 9th, and 11th passages: all 0%). Thus, the cell population comprising the fetal appendage-derived mesenchymal stem cells obtained by the method of the present invention was found to have mesenchymal stem cells positive for the monocyte marker CD14 and to have only a very small amount of mesenchymal stem cells positive for the fetal-specific marker CD200.

The culture of the amniotic MSCs of the 11th passage was further continued by the culture method described above. As a result, the amniotic MSCs were culturable without the arrest of proliferation at least up to 107 days as the total number of culture days and a population doubling level of 43. A growth curve was also prepared as to the amniotic MSCs thus cultured in the same way as in "Culture of amniotic MSCs; usual culture" (culture of the present invention (bFGF+) in FIG. 6). The population doubling time at the 7th passage was 1.6 days, the population doubling time at the 9th passage was 1.3 days, and the population doubling time at the 11th passage was 1.4 days. These results demonstrated that amniotic MSCs that satisfy conditions involving the positive rate of CD105 which is 50% or more, the positive rate of CD200 which is less than 10%, the positive rate of CD14 which is 5% or more, and the positive rate of CD106 which is less than 5% are highly proliferative and also have a population doubling time of 2.0 days or shorter, irrespective of a culture method.

The addition of bFGF to the medium decreased the positive rate of CD200 (FIGS. 3 to 5) and also improved the proliferative properties of amniotic MSCs, as compared with an aspect without the addition of bFGF. This suggested that particularly, the positive rate of CD200 among various surface antigens is involved in the proliferative properties of amniotic MSCs.

In the present invention, it was found that a cell population comprising highly proliferative mesenchymal stem cells can be obtained in any case by a culture method that satisfies conditions that maintain the positive rate of CD105 which is 50% or more, the positive rate of CD200 which is less than 10%, the positive rate of CD14 which is 5% or more, and the positive rate of CD106 which is less than 5%. Specifically, the present invention demonstrated that the proliferative properties of mesenchymal stem cells can be monitored by measuring, as an index, the positive rate of CD105 which is 50% or more, the positive rate of CD200 which is less than 10%, the positive rate of CD14 which is 5% or more, and the positive rate of CD106 which is less than 5% (preferably over time) in a cell population comprising mesenchymal stem cells.

In this assay, the antibodies for isotype control used was PE Mouse IgG1, κ Isotype Control (Becton, Dickinson and Company/model number: 555749), FITC Mouse IgG1, κ Isotype Control (Becton, Dickinson and Company/model number: 550616), and FITC Mouse IgG2a, κ Isotype Control, REA Control (S)-PE isotype control antibody (Miltenyi Biotec/130-104-612). The antibody against the CD73 antigen used was PE Mouse Anti-Human CD73 (Becton, Dickinson and Company/model number: 550257). The antibody against the CD90 antigen used was FITC Mouse Anti-Human CD90 (Becton, Dickinson and Company/model number: 555595). The antibody against the CD105 antigen used was Anti-Human Antibodies FITC Conjugate (Ancell Corp./model number: 326-040). The antibody against the CD14 antigen used was FITC Mouse Anti-Human CD14 (Becton, Dickinson and Company/model number: 555397). The antibody against the CD45 antigen used was FITC Mouse Anti-Human CD45 (Becton, Dickinson and Company/model number: 555482). The antibody against the CD200 antigen used was PE Mouse Anti-Human CD200 (Becton, Dickinson and Company/model number: 561762). The antibody against the CD106 antigen used was CD106-PE, human monoclonal (Miltenyi Biotec/130-104-163).

The measurement of cells and the calculation of the proportions of positive cells were performed by the same procedures as in the above "Step 1-2: Enzyme treatment of amnion and recovery of amniotic MSCs".

Example 3: Monitoring of Proliferative Properties of Amniotic MSCs

The amnion comprising an epithelial cell layer and a mesenchymal stem cell layer, obtained in the above "Step 1-1: Collection of amnion" was dipped in a Hank's balanced salt solution (containing Ca and Mg) containing 240 PU/mL collagenase and 200 PU/mL dispase I. The amnion was enzyme-treated by shaking and stirring under conditions of 37° C., 90 minutes, and 50 rpm. The solution thus enzyme-treated was filtered through a nylon mesh having openings of 95 μm for the removal of undigested products of the amnion to recover a cell suspension containing amniotic MSCs. This cell suspension was seeded at a density of 6,000 cells/cm$^2$ to CellStack and cultured until subconfluent in αMEM (alpha modification of minimum essential medium Eagle) containing 10% fetal bovine serum (FBS) and 10 ng/mL basic fibroblast growth factor (bFGF) (both in terms of final concentration). Then, the cells of the 1st passage were dissociated using TrypLE Select. A ⅕ amount of the cells was seeded to CellStack at the same scale as that of the preceding culture and thereby subcultured. Medium replacement was carried out with a frequency of once 2 to 4 days. At the time of reaching subconfluence, the cells of the 2nd passage were dissociated using TrypLE Select. RPMI1640 was added thereto such that the cell concentration was $2 \times 10^7$ cells/mL. CP-1 solution (mixed solution at a ratio of CP-1: 25% human serum albumin=34:16) was added in an amount equal thereto. The mixture was transferred to a cryovial, slowly frozen to −80° C., and then cryopreserved under liquid nitrogen for 1 day. After subsequent thawing, the cells of the 3rd passage were seeded at a density of approximately 18,000 cells/cm$^2$ to CellStack and cultured until subconfluent in αMEM (alpha modification of minimum essential medium Eagle) containing 10% fetal bovine serum (FBS) and 10 ng/mL basic fibroblast growth factor (bFGF) (both in terms of final concentration). Then, the cells of the 3rd passage were dissociated using TrypLE Select. A ⅕ amount of the cells was seeded to CellStack at the same scale as that of the preceding culture and thereby subcultured. Medium replacement was carried out with a frequency of once 2 to 4 days. At the time of reaching subconfluence, the cells of the 4th passage were dissociated using TrypLE Select. RPMI1640 was added thereto such that the cell concentration was $4 \times 10^6$ cells/mL. CP-1 solution (mixed solution at a ratio of CP-1:25% human serum albumin=34:16) was added in an amount equal thereto. The mixture was transferred to a cryovial, slowly frozen to −80° C., and then cryopreserved under liquid nitrogen for 1 day. After subsequent thawing, the cells of the 5th passage were seeded at a density of approximately 6,000 cells/cm$^2$ to CellStack and cultured until subconfluent in αMEM (alpha modification of minimum essential medium Eagle) containing 10% fetal bovine serum (FBS) and 10 ng/mL basic fibroblast growth factor (bFGF) (both in terms of final concentration). Then, the cells of the 5th passage were dissociated using TrypLE Select. A ⅕ amount of the cells was seeded to CellStack at the same scale as that of the preceding culture and thereby subcultured. Medium replacement was carried out with a frequency of once 2 to 4 days. At the time of reaching subconfluence, the cells of the 6th passage were dissociated using TrypLE Select. RPMI1640 was added thereto such that the cell concentration was $4 \times 10^6$ cells/mL. CP-1 solution (mixed solution at a ratio of CP-1:25% human serum albumin=34:16) was added in an amount equal thereto. The mixture was transferred to a cryovial, slowly frozen to −80° C., and then cryopreserved under liquid nitrogen. All the cells of the 7th passage or later were seeded at a density of approximately 6,000 cells/cm$^2$ to CellStack and cultured until subconfluent in αMEM (alpha modification of minimum essential medium Eagle) containing 10% fetal bovine serum (FBS) and 10 ng/mL basic fibroblast growth factor (bFGF) (both in terms of final concentration). Then, the cells were dissociated using TrypLE Select. Subculture was repeated until the 10th passage. The amniotic MSCs of the 2nd, 4th, 6th, 8th, and 10th passages cultured by the culture method described above were analyzed for the proportions of cells positive for various surface antigens (CD73, CD90, CD105, CD45, CD106, and CD200 known as amniotic MSC markers) using a flow cytometer (FIG. 8). As a result, the positive rate of CD105 was 50% or more at any passage number (specifically, 2nd passage: 98%, 4th passage: 99%, 6th passage: 99%, 8th passage: 99%, 10th passage: 99%). The positive rate of CD200 was 10% or more up to the 4th passage and less than 10% at the 6th passage or later (specifically, 2nd passage: 77%, 4th passage: 32%, 6th passage: 2%, 8th passage: 1%, 10th passage: 0%). The positive rate of CD106 was 5% or more up to the 4th passage and less than 5% at the 6th passage or later (specifically, 2nd passage: 14%, 4th passage: 7%, 6th passage: 3%, 8th passage: 0%, 10th passage: 0%). A growth curve was also prepared as to the amniotic MSCs thus cultured in the same way as in "Step 1-3: Culture of amniotic MSCs; usual culture" (FIG. 9). As a result of calculating a population doubling time, the population doubling time at the 2nd passage was 2.9 days, the population doubling time at the 4th passage was 5 days, the population doubling time at the 6th passage was 1.3 days, the population doubling time at the 8th passage was 1.3 days, and the population doubling time at the 10th passage was 1.6 days. These results demonstrated that amniotic MSCs (specifically, amniotic MSCs of the 6th passage or later) that satisfy conditions involving the positive rate of CD105 which is 50% or more, the positive rate of CD200 which is less than 10%, and the positive rate of CD106 which is less than 5% are highly proliferative and also have a population doubling time of 2 days or shorter. On the other hand, these results also indicated that amniotic MSCs (specifically, amniotic MSCs of the 2nd and 4th passages) that do not satisfy the conditions are low proliferative and also have a population doubling time exceeding 2 days.

Specifically, the present invention demonstrated that the proliferative properties of mesenchymal stem cells can be monitored by utilizing, as an index, the proportion of CD105$^+$ mesenchymal stem cells which is 50% or more in a cell population comprising mesenchymal stem cells, the proportion of CD200+ mesenchymal stem cells in the cell population which is less than 10%, and the proportion of CD106+ mesenchymal stem cells in the cell population which is less than 5%, and measuring the positive rate of each surface antigen in the mesenchymal stem cells over time. The present invention also demonstrated that when low proliferative properties are determined from the measurement results of the index, the proliferative properties of the mesenchymal stem cells can be improved by properly changing culture conditions. In this assay, the antibodies for isotype control used were PE Mouse IgG1, κ Isotype Control (Becton, Dickinson and Company/model number: 555749), FITC Mouse IgG1, κ Isotype Control (Becton, Dickinson and Company/model number: 550616), and FITC Mouse IgG2a, κ Isotype Control (Becton, Dickinson and Company/model number: 555573). The antibody against the CD73 antigen used was FITC Mouse Anti-Human CD73 (Becton, Dickinson and Company/model number: 561254). The antibody against the CD90 antigen used was FITC Mouse Anti-Human CD90 (Becton, Dickinson and Company/model number: 555595). The antibody against the CD105 antigen used was Anti-Human Antibodies FITC Conjugate (BioLegend, Inc./model number: 323203). The antibody against the CD45 antigen used was FITC Mouse Anti-Human CD45 (Becton, Dickinson and Company/model number: 555482). The antibody against the CD200 antigen used was PE Mouse Anti-Human CD200 (Becton, Dickinson and Company/model number: 552475). The antibody against the CD106 antigen used was FITC Mouse Anti-Human CD106 (Becton, Dickinson and Company/model number: 551146). The measurement of cells and the calculation of the proportions of positive cells were performed by the same procedures as in the above "Step 1-2: Enzyme treatment of amnion and recovery of amniotic MSCs".

Example 4: Study on Immunomodulatory Effect of Amniotic MSCs

The amniotic MSCs cultured in the above "Example 1: Culture of amniotic MSCs (culture according to present invention)" were seeded at a density of $1.5 \times 10^4$ cells/cm$^2$ to a plastic culture vessel and cultured for 6 hours in RPMI1640 medium containing 10% FBS and 20 μM 2-mercaptoethanol. To the cultured amniotic MSCs, human peripheral mononuclear cells (PBMCs) were seeded at a density of $1.5 \times 10^5$ cells/cm$^2$, and these cells were cocultured. Also, human PBMCs were cultured alone at a density of $1.5 \times 10^5$ cells/cm$^2$. Further, at the same time therewith, the coculture of the amniotic MSCs and the human PBMCs or the culture of the human PBMCs alone was performed by the addition of 2.5 μg/mL (final concentration) phytohemagglutinin (PHA) in order to enhance the proliferative activity of the human PBMCs. After each culture for 48 hours, the cell-proliferative activity of each cell population was evaluated using Click-iT EdU Microplate Assay kit (Thermo Fisher Scientific Inc.). The evaluation of the cell-proliferative activity was carried out according to the Click-iT EdU Microplate Assay kit by measuring fluorescence intensity at wavelengths of 568 nm for excitation light and 585 nm for fluorescence. The results are shown in FIG. 10. The unit on the ordinate of FIG. 10 is the fluorescence intensity at wavelengths of 568 nm for excitation light and 585 nm for fluorescence. The amniotic MSCs suppressed the proliferative activity of activated human PBMCs (FIG. 10).

Example 5: Study on Enzyme Treatment Method

The cell population comprising the amniotic MSCs obtained in the above "Step 1-2: Enzyme treatment of amnion and recovery of amniotic MSCs" was cultured by the method described in claim 7 and paragraph 0045<Preparation of cell population of amniotic mesenchymal cells> of WO2013/077428. Specifically, the cell population comprising the amniotic MSCs was seeded at a density of approximately 10,000 cells/cm$^2$ to a plastic culture vessel and cultured for 3 days in αMEM (alpha modification of minimum essential medium Eagle) containing 10% fetal bovine serum (FBS) (initial culture). Three days later, the amniotic MSCs were passaged at a density of 500 cells/cm$^2$ and cultured for 1 week. Then, subculture was repeated at a density of 500 cells/cm$^2$. After confirmation that amniotic MSCs having a fusiform form were purified to some extent, subculture was performed at a usual density (approximately 5,000 to 10,000 cells). A growth curve was also prepared as to the amniotic MSCs thus cultured in the same way as in "Step 1-3: Culture of amniotic MSCs; usual culture" (FIG. 11).

The culture curve thus obtained (FIG. 11) was compared with FIG. 4(d) of WO2013/077428. The amniotic MSCs obtained above and the amniotic MSCs obtained by the method of claim 7 and paragraph 0045 of WO2013/077428 differed only in enzyme treatment conditions and were both subjected to the same culture method after the enzyme treatment. In spite of the same culture method, the number of culture days on the order of 60 days is necessary for the number of times of cell division (population doubling level) of 10 in WO2013/077428, whereas the population doubling level reached 10 in the number of culture days on the order of 30 days for the enzyme treatment method according to the present invention (FIG. 11). Specifically, the amniotic MSCs enzyme-treated under the conditions of the present invention were highly proliferative as compared with the amniotic MSCs enzyme-treated under the conditions described in WO2013/077428.

The amniotic MSCs of the 9th passage enzyme-treated by the method of Example 5 and cultured by the culture method were analyzed for the proportions of cells positive for various surface antigens (CD73, CD90, CD105, CD44, CD166, CD45, CD326, and CD14 known as amniotic MSC markers) using a flow cytometer (FIG. 12). As a result, the positive rate of CD105 was 50% or more (specifically 86%), and the positive rate of CD14 was 5% or more (specifically 12%).

According to the present invention, the positive rate of CD105 which is 50% or more, the positive rate of CD200 which is less than 10%, the positive rate of CD14 which is 5% or more, and the positive rate of CD106 which is less than 5% can be utilized as an index for determining and/or predicting optimum enzyme treatment conditions. Thus, a sample having a high content of highly proliferative MSCs can be selected in advance. This enables reduction in production cost and can shorten a culture period of time.

Example 6: Quality Evaluation of Sample Collected from Donor

A fetal membrane and a placenta are aseptically collected as the fetal appendage from three pregnant women who are an elective cesarean section case after the obtaining of informed consent. The fetal appendage from each woman is treated according to "Step 1-1: Collection of amnion" and "Step 1-2: Enzyme treatment of amnion and recovery of amniotic MSCs" to obtain amniotic MSCs. The amniotic MSCs obtained from the fetal appendages of the three subjects are designated as #1, #2, and #3, respectively. The cell populations comprising the amniotic MSCs #1, #2, and #3 thus obtained are each cultured by the method of "Example 1: Culture of amniotic MSCs (culture according to present invention)".

The amniotic MSCs cultured by the culture method described above can be analyzed for the proportions of cells positive for various surface antigens using a flow cytometer. A growth curve can also be prepared as to the amniotic MSCs cultured by the culture method described above in the same way as in "Step 1-3: Culture of amniotic MSCs; usual culture".

In this way, the quality of a donor itself and a sample collected from the donor can be evaluated by examining the positive rates of CD105, CD200, CD106 and CD14 in the amniotic MSCs #1, #2, and #3 differing in donor. According to the present invention, the quality of a donor itself and a sample collected from the donor can be evaluated by utilizing, as an index, the positive rate of CD105 which is 50% or more, the positive rate of CD200 which is less than 10%, the positive rate of CD14 which is 5% or more, and the positive rate of CD106 which is less than 5%. Thus, a sample having a high content of highly proliferative MSCs can be selected in advance. This enables reduction in production cost and can shorten a culture period of time.

Example 7: Quality Evaluation of Samples Collected from Different Donors

A fetal membrane and a placenta were aseptically collected as the fetal appendage from two pregnant women who were an elective cesarean section case after the obtaining of informed consent. The fetal appendage from each woman was treated according to Example 3 to obtain amniotic MSCs. The amniotic MSCs obtained from the fetal appendages of the two subjects were designated as #4 and #5, respectively. The cell populations comprising the amniotic MSCs #4 and #5 thus obtained were each cultured up to the 6th passage in the same way as the method of Example 3. The amniotic MSCs of the 6th passage were analyzed for the proportions of cells positive for various surface antigens (CD73, CD90, CD105, CD45, CD106, CD200, and CD14 known as amniotic MSC markers) using a flow cytometer (FIG. 13). In the amniotic MSCs #4, the positive rate of CD105 was 99%, the positive rate of CD200 was 2%, the positive rate of CD106 was 3%, and the positive rate of CD14 was 7%. On the other hand, in the amniotic MSCs #5, the positive rate of CD105 was 99%, the positive rate of CD200 was 32%, the positive rate of CD106 was 38%, and the positive rate of CD14 was 11%. When the population doubling time of the amniotic MSCs at the 6th passage was compared between #4 and #5, the population doubling time of the amniotic MSCs #4 was 2 days or shorter (specifically 1.3 days), whereas the population doubling time of the amniotic MSCs #5 exceeded 2 days (specifically 2.7 days) and was thus found to be slower by two or more times than that of the amniotic MSCs #4. A growth curve was also prepared as to the amniotic MSCs #4 and #5 in the same way as in "Step 1-3: Culture of amniotic MSCs; usual culture" (FIG. 14). As a result, the amniotic MSCs #4 exhibited higher proliferative properties. These results indicated that amniotic MSCs obtained from different donors differ largely in proliferative properties even if the amniotic MSCs are collected and cultured from amnions by the same method, and suggested that the quality of a donor itself and a sample collected from the donor can be evaluated by examining the positive rates of CD105, CD200, CD106 and CD14. According to the present invention, the quality of a donor itself and a sample collected from the donor can be evaluated by utilizing, as an index, the positive rate of CD105 which is 50% or more, the positive rate of CD200 which is less than 10%, and the positive rate of CD106 which is less than 5%. Thus, a sample having a high content of highly proliferative MSCs can be selected.

Example 8: Production of Pharmaceutical Composition

A portion of the amniotic MSCs obtained in the above "Example 1: Culture of amniotic MSCs (culture according to present invention)" is subjected to the preparation of a pharmaceutical composition. A pharmaceutical composition (cell preparation) comprising 25 mL of RPMI1640 medium containing $2.3 \times 10^8$ amniotic MSCs, 0.50 g of dextran, 1.3 g of DMSO and 1.0 g of human serum albumin is prepared. The pharmaceutical composition is enclosed in a bag for freezing and preserved in a frozen state. The pharmaceutical composition can be thawed upon use and applied to a patient.

The invention claimed is:

1. A method for producing a cell population comprising mesenchymal stem cells derived from the fetal appendage, the method comprising a step of
   identifying a cell population comprising cells collected from a fetal appendage having a proportion of $CD105^+$ mesenchymal stem cells is 50% or more, a proportion of $CD200^+$ mesenchymal stem cells is less than 10%, and a proportion of $CD106^+$ mesenchymal stem cells is less than 5%,
   treating the cell population comprising the cells collected from the fetal appendage with collagenase and metalloproteinase, and
   culturing the cell population comprising the cells collected from the fetal appendage under conditions that maintain the proportion of $CD105^+$ mesenchymal stem cells in the cell population which is 50% or more, the proportion of $CD200^+$ mesenchymal stem cells in the cell population which is less than 10%, and the proportion of $CD106^+$ mesenchymal stem cells in the cell population which is less than 5%.

2. The method for producing a cell population according to claim 1, wherein the cell population comprising cells collected from the fetal appendage is a cell population obtained by treating a sample comprising an epithelial cell layer and a mesenchymal stem cell layer collected from the fetal appendage with collagenase and metalloproteinase.

3. The method for producing a cell population according to claim 1, further comprising a step of repeating a plurality of times seeding of the cell population comprising cells collected from the fetal appendage at a density of 400 to 5,000 cells/cm$^2$, followed by culture.

4. The method for producing a cell population according to claim 3, wherein the culture period of time is 4 to 10 days.

* * * * *